United States Patent
Jimenez

(10) Patent No.: US 9,867,717 B2
(45) Date of Patent: Jan. 16, 2018

(54) STABLE DEVICE FOR INTERVERTEBRAL DISTRACTION AND FUSION

(71) Applicant: Ex Technology, LLC, Gering, NE (US)

(72) Inventor: Omar F. Jimenez, Gering, NE (US)

(73) Assignee: Ex Technology, LLC, Gering, NE (US)

( * ) Notice: Subject to any disclaimer, the term of this patent is extended or adjusted under 35 U.S.C. 154(b) by 631 days.

(21) Appl. No.: 14/153,281

(22) Filed: Jan. 13, 2014

(65) Prior Publication Data
US 2014/0194991 A1 Jul. 10, 2014

Related U.S. Application Data

(63) Continuation of application No. 12/407,608, filed on Mar. 19, 2009, now Pat. No. 8,628,577.

(51) Int. Cl.
*A61F 2/44* (2006.01)
*A61F 2/46* (2006.01)
(Continued)

(52) U.S. Cl.
CPC ............ *A61F 2/447* (2013.01); *A61F 2/442* (2013.01); *A61F 2/4611* (2013.01);
(Continued)

(58) Field of Classification Search
CPC . A61F 2220/0025; A61F 2/442; A61F 2/3099
(Continued)

(56) References Cited

U.S. PATENT DOCUMENTS 283,218 A  8/1883  Rycke
703,251 A  6/1902  Haire
(Continued)

FOREIGN PATENT DOCUMENTS

EP  1342456 A1  9/2003
EP  1552797 A2  7/2005
(Continued)

OTHER PUBLICATIONS

PCT/US2010/042941, filed Jul. 22, 2010, International Search Report and Written Opinion, dated Apr. 25, 2011.
(Continued)

*Primary Examiner* — Christine Nelson
(74) *Attorney, Agent, or Firm* — Patterson Thuente Pedersen, P.A.

(57) ABSTRACT

Improved methods and apparatuses for vertebral body distraction and fusion in accordance with various embodiments employ mechanisms for stabilizing a device so that the device can stay in the body and stably support the disc space during vertebral fusion following distraction of the adjacent vertebra by operation of the device. The device is inserted into the disc space and distracted from a compressed configuration to an expanded configuration to distract the disc space. Mechanisms for stabilizing the device in the expanded configuration constrain the device to zero degrees of freedom of movement to allow the device to stably support the disc space. A bone growth stimulant for promoting vertebral fusion can be inserted into an open space defined by the device, which continues to stably support the disc space during vertebral fusion.

17 Claims, 17 Drawing Sheets

(51) Int. Cl.
 *A61F 2/30* (2006.01)
 *A61F 2/28* (2006.01)
 *A61F 2/48* (2006.01)
(52) U.S. Cl.
 CPC ... *A61F 2/30965* (2013.01); *A61F 2002/2817* (2013.01); *A61F 2002/2835* (2013.01); *A61F 2002/30087* (2013.01); *A61F 2002/30092* (2013.01); *A61F 2002/30364* (2013.01); *A61F 2002/30367* (2013.01); *A61F 2002/30471* (2013.01); *A61F 2002/30507* (2013.01); *A61F 2002/30509* (2013.01); *A61F 2002/30522* (2013.01); *A61F 2002/30523* (2013.01); *A61F 2002/30525* (2013.01); *A61F 2002/30556* (2013.01); *A61F 2002/30601* (2013.01); *A61F 2002/30616* (2013.01); *A61F 2002/30629* (2013.01); *A61F 2002/30637* (2013.01); *A61F 2002/30777* (2013.01); *A61F 2002/30827* (2013.01); *A61F 2002/30841* (2013.01); *A61F 2002/30843* (2013.01); *A61F 2002/4475* (2013.01); *A61F 2002/482* (2013.01); *A61F 2310/00017* (2013.01); *A61F 2310/00023* (2013.01)
(58) Field of Classification Search
 USPC ............................... 623/17.15, 17.16, 17.17
 See application file for complete search history.

(56) References Cited

U.S. PATENT DOCUMENTS

| | | |
|---|---|---|
| 811,344 A | 1/1906 | Wands |
| 1,388,836 A | 8/1921 | Ripsch et al. |
| 1,500,859 A | 7/1924 | Wright |
| 1,547,946 A | 7/1925 | Myers |
| 2,106,088 A | 1/1938 | De Tar |
| 2,231,221 A | 2/1941 | Rector |
| 2,453,656 A | 11/1948 | Bullard, III |
| 2,666,334 A | 1/1954 | Nalle |
| 2,711,105 A | 6/1955 | Williams |
| 2,842,976 A | 7/1958 | Young |
| 2,891,408 A | 6/1959 | Burt, Jr. |
| 3,386,128 A | 6/1968 | Vyvyan |
| 3,449,971 A | 6/1969 | Posh |
| 3,575,475 A | 4/1971 | Boerner |
| 3,596,863 A | 8/1971 | Kaspareck |
| 3,597,938 A | 8/1971 | Hellen |
| 3,700,289 A | 10/1972 | Bilinski et al. |
| 3,700,290 A | 10/1972 | Ensinger |
| 3,708,925 A | 1/1973 | Ainoura |
| 3,709,132 A | 1/1973 | Farrell et al. |
| 3,916,596 A | 11/1975 | Hawley |
| 3,985,000 A | 10/1976 | Hartz |
| 3,988,906 A | 11/1976 | Smith |
| 4,261,211 A | 4/1981 | Haberland |
| 4,396,047 A | 8/1983 | Balkus |
| 4,478,109 A | 10/1984 | Kobelt |
| 4,516,303 A | 5/1985 | Kloster |
| 4,528,864 A | 7/1985 | Craig |
| 4,559,717 A | 12/1985 | Scire et al. |
| 4,630,495 A | 12/1986 | Smith |
| 4,691,586 A | 9/1987 | van Leijenhorst et al. |
| 4,694,703 A | 9/1987 | Routson |
| 4,869,552 A | 9/1989 | Tolleson et al. |
| 5,133,108 A | 7/1992 | Esnault |
| 5,172,442 A | 12/1992 | Bartley et al. |
| 5,181,371 A | 1/1993 | Deworth |
| 5,196,857 A | 3/1993 | Chiappetta et al. |
| 5,198,932 A | 3/1993 | Takamura |
| 5,222,986 A | 6/1993 | Wright |
| 5,313,852 A | 5/1994 | Arena |
| 5,374,556 A | 12/1994 | Bennett et al. |
| 5,439,377 A | 8/1995 | Milanovich |
| 5,445,471 A | 8/1995 | Wexler et al. |
| 5,554,191 A | 9/1996 | Lahille et al. |
| 5,645,599 A | 7/1997 | Samani |
| 5,653,763 A * | 8/1997 | Errico .................... A61F 2/446 411/55 |
| 5,664,457 A | 9/1997 | Nejati |
| 5,904,479 A | 5/1999 | Staples |
| 5,960,670 A | 10/1999 | Iverson et al. |
| 5,980,252 A | 11/1999 | Samchukov et al. |
| 5,988,006 A | 11/1999 | Fleytman |
| 6,039,761 A | 3/2000 | Li et al. |
| 6,045,579 A | 4/2000 | Hochshuler et al. |
| 6,056,491 A | 5/2000 | Hsu |
| 6,080,193 A | 6/2000 | Hochshuler et al. |
| 6,136,031 A | 10/2000 | Middleton |
| 6,175,989 B1 | 1/2001 | Carpentar et al. |
| 6,315,797 B1 | 11/2001 | Middleton |
| 6,350,317 B1 | 2/2002 | Hao et al. |
| 6,378,172 B1 | 4/2002 | Schrage |
| 6,395,035 B2 | 5/2002 | Bresina et al. |
| 6,454,806 B1 | 9/2002 | Cohen et al. |
| 6,454,807 B1 | 9/2002 | Jackson |
| 6,484,608 B1 | 11/2002 | Ziavras |
| 6,517,772 B1 | 2/2003 | Woolf |
| 6,554,526 B1 | 4/2003 | Egelandsdal |
| 6,616,695 B1 | 9/2003 | Crozet et al. |
| 6,641,614 B1 | 11/2003 | Wagner et al. |
| 6,719,796 B2 | 4/2004 | Cohen et al. |
| 6,752,832 B2 | 6/2004 | Neumann |
| 6,772,479 B2 | 8/2004 | Hinkley et al. |
| 6,802,229 B1 | 10/2004 | Lambert |
| 6,808,537 B2 | 10/2004 | Michelson |
| 6,863,673 B2 | 3/2005 | Gerbec et al. |
| 6,932,844 B2 | 8/2005 | Ralph et al. |
| 6,953,477 B2 | 10/2005 | Berry |
| 7,018,415 B1 | 3/2006 | McKay |
| 7,051,610 B2 | 5/2006 | Stoianovici et al. |
| 7,070,598 B2 | 7/2006 | Lim et al. |
| 7,087,055 B2 | 8/2006 | Lim et al. |
| 7,201,751 B2 | 4/2007 | Zucherman et al. |
| 7,273,373 B2 | 9/2007 | Horiuchi |
| 7,308,747 B2 | 12/2007 | Smith et al. |
| 7,316,381 B2 | 1/2008 | Häcker et al. |
| 7,410,201 B1 | 8/2008 | Wilson et al. |
| 7,425,103 B2 | 9/2008 | Perez-Sanchez |
| 7,431,735 B2 | 10/2008 | Liu et al. |
| 7,435,032 B1 | 10/2008 | Murphey et al. |
| 7,547,325 B2 | 6/2009 | Biedermann et al. |
| 7,584,682 B2 | 9/2009 | Hsiao |
| 7,611,538 B2 | 11/2009 | Belliard et al. |
| 7,632,281 B2 | 12/2009 | Errico et al. |
| 7,674,296 B2 | 3/2010 | Rhoda et al. |
| 7,682,376 B2 | 3/2010 | Trieu |
| 7,708,779 B2 | 5/2010 | Edie et al. |
| 7,712,389 B2 | 5/2010 | Wang |
| 7,753,958 B2 | 7/2010 | Gordon et al. |
| 7,758,645 B2 | 7/2010 | Studer |
| 7,758,648 B2 | 7/2010 | Castleman et al. |
| 7,892,285 B2 | 2/2011 | Viker |
| 7,896,919 B2 | 3/2011 | Belliard et al. |
| 7,901,409 B2 | 3/2011 | Canaveral et al. |
| 7,947,078 B2 | 5/2011 | Siegal |
| 7,985,256 B2 | 7/2011 | Grotz et al. |
| 8,057,549 B2 | 11/2011 | Butterman et al. |
| 8,070,813 B2 | 12/2011 | Grotz et al. |
| 8,088,163 B1 | 1/2012 | Kleiner |
| 8,192,495 B2 | 6/2012 | Simpson et al. |
| 8,303,663 B2 | 11/2012 | Jimenez et al. |
| 8,496,706 B2 | 7/2013 | Ragab et al. |
| 8,523,944 B2 | 9/2013 | Jimenez et al. |
| 8,540,452 B2 | 9/2013 | Jimenez et al. |
| 8,628,577 B1 | 1/2014 | Jimenez |
| 8,636,746 B2 | 1/2014 | Jimenez et al. |
| 8,771,360 B2 | 7/2014 | Jimenez et al. |
| 8,795,366 B2 | 8/2014 | Varela |
| 8,894,712 B2 | 11/2014 | Varela |
| 8,906,100 B2 | 12/2014 | Jimenez |
| 8,932,302 B2 | 1/2015 | Jimenez et al. |
| 8,940,049 B1 | 1/2015 | Jimenez et al. |

(56) References Cited

U.S. PATENT DOCUMENTS

| | | |
|---|---|---|
| 9,358,125 B2 | 6/2016 | Jimenez et al. |
| 9,474,626 B2 | 10/2016 | Jimenez |
| 9,486,328 B2 | 11/2016 | Jimenez |
| 9,498,270 B2 | 11/2016 | Jimenez |
| 9,668,879 B2 | 6/2017 | Jimenez et al. |
| 2002/0128716 A1 | 9/2002 | Cohen et al. |
| 2002/0138146 A1* | 9/2002 | Jackson ............... A61F 2/4455 623/17.15 |
| 2003/0077110 A1 | 4/2003 | Knowles |
| 2003/0233145 A1 | 12/2003 | Landry et al. |
| 2004/0049271 A1 | 3/2004 | Biedermann et al. |
| 2004/0111157 A1 | 6/2004 | Ralph et al. |
| 2004/0153156 A1 | 8/2004 | Cohen et al. |
| 2004/0193158 A1 | 9/2004 | Lim |
| 2004/0225364 A1 | 11/2004 | Richelsoph et al. |
| 2005/0000228 A1 | 1/2005 | De Sousa et al. |
| 2005/0033431 A1 | 2/2005 | Gordon et al. |
| 2005/0095384 A1 | 5/2005 | Wittmeyer, Jr. |
| 2005/0113921 A1 | 5/2005 | An et al. |
| 2005/0113924 A1 | 5/2005 | Buttermann |
| 2005/0175406 A1 | 8/2005 | Perez-Sanchez |
| 2005/0182416 A1* | 8/2005 | Lim ...................... A61B 17/025 606/90 |
| 2005/0261769 A1 | 11/2005 | Moskowitz et al. |
| 2006/0004447 A1 | 1/2006 | Mastrorio et al. |
| 2006/0004455 A1 | 1/2006 | Leonard et al. |
| 2006/0025862 A1 | 2/2006 | Villiers et al. |
| 2006/0058878 A1 | 3/2006 | Michelson |
| 2006/0129244 A1 | 6/2006 | Ensign |
| 2006/0149385 A1 | 7/2006 | McKay |
| 2006/0184171 A1 | 8/2006 | Biedermann et al. |
| 2006/0247781 A1 | 11/2006 | Francis |
| 2006/0253201 A1 | 11/2006 | McLuen |
| 2006/0293752 A1 | 12/2006 | Mounmene et al. |
| 2007/0032791 A1 | 2/2007 | Greenhalgh et al. |
| 2007/0049943 A1 | 3/2007 | Moskowitz et al. |
| 2007/0083267 A1 | 4/2007 | Miz et al. |
| 2007/0093901 A1 | 4/2007 | Grotz et al. |
| 2007/0129730 A1 | 6/2007 | Woods et al. |
| 2007/0173826 A1 | 7/2007 | Canaveral |
| 2007/0185577 A1 | 8/2007 | Malek |
| 2007/0191954 A1 | 8/2007 | Hansell et al. |
| 2007/0191958 A1 | 8/2007 | Abdou |
| 2007/0198089 A1 | 8/2007 | Moskowitz et al. |
| 2007/0219634 A1 | 9/2007 | Greenhalgh et al. |
| 2007/0222100 A1 | 9/2007 | Husted et al. |
| 2007/0250171 A1 | 10/2007 | Bonin, Jr. |
| 2007/0255415 A1 | 11/2007 | Edie et al. |
| 2007/0282449 A1 | 12/2007 | de Villiers et al. |
| 2007/0288092 A1 | 12/2007 | Bambakidis |
| 2007/0293329 A1 | 12/2007 | Glimpel et al. |
| 2007/0293948 A1 | 12/2007 | Bagga et al. |
| 2008/0026903 A1 | 1/2008 | Flugrad et al. |
| 2008/0077246 A1 | 3/2008 | Fehling et al. |
| 2008/0091211 A1 | 4/2008 | Gately |
| 2008/0100179 A1 | 5/2008 | Ruggeri et al. |
| 2008/0103601 A1 | 5/2008 | Biro et al. |
| 2008/0114367 A1 | 5/2008 | Meyer |
| 2008/0140207 A1 | 6/2008 | Olmos |
| 2008/0147194 A1 | 6/2008 | Grotz et al. |
| 2008/0154266 A1 | 6/2008 | Protopsaltis et al. |
| 2008/0161920 A1 | 7/2008 | Melkent |
| 2008/0161931 A1 | 7/2008 | Perez-Cruet et al. |
| 2008/0168855 A1 | 7/2008 | Giefer et al. |
| 2008/0183204 A1 | 7/2008 | Greenhalgh et al. |
| 2008/0188941 A1 | 8/2008 | Grotz |
| 2008/0210039 A1 | 9/2008 | Brun |
| 2008/0221694 A1 | 9/2008 | Warnick et al. |
| 2008/0234736 A1 | 9/2008 | Trieu et al. |
| 2008/0281423 A1 | 11/2008 | Sheffer et al. |
| 2008/0292392 A1 | 11/2008 | Voellmer |
| 2008/0319487 A1 | 12/2008 | Fielding et al. |
| 2009/0012564 A1 | 1/2009 | Chirico et al. |
| 2009/0076614 A1 | 3/2009 | Arramon |
| 2009/0099568 A1 | 4/2009 | Lowry et al. |
| 2009/0164017 A1 | 6/2009 | Sommerich et al. |
| 2009/0210061 A1 | 8/2009 | Sledge |
| 2009/0222100 A1 | 9/2009 | Cipoletti et al. |
| 2009/0234362 A1 | 9/2009 | Blain et al. |
| 2009/0259316 A1 | 10/2009 | Ginn et al. |
| 2009/0299478 A1 | 12/2009 | Carls et al. |
| 2009/0306672 A1 | 12/2009 | Reindel et al. |
| 2010/0004688 A1 | 1/2010 | Maas et al. |
| 2010/0076557 A1 | 3/2010 | Miller |
| 2010/0082109 A1 | 4/2010 | Greenhalgh et al. |
| 2010/0094305 A1 | 4/2010 | Chang et al. |
| 2010/0161062 A1 | 6/2010 | Foley et al. |
| 2010/0185291 A1 | 7/2010 | Jimenez et al. |
| 2010/0192715 A1 | 8/2010 | Vauchel et al. |
| 2010/0209184 A1 | 8/2010 | Jimenez et al. |
| 2011/0015638 A1 | 1/2011 | Pischl et al. |
| 2011/0054616 A1 | 3/2011 | Kamran et al. |
| 2011/0093075 A1 | 4/2011 | Duplessis et al. |
| 2011/0112644 A1 | 5/2011 | Zilberstein et al. |
| 2011/0138948 A1 | 6/2011 | Jimenez et al. |
| 2011/0160861 A1 | 6/2011 | Jimenez et al. |
| 2011/0172774 A1 | 7/2011 | Varela |
| 2011/0270398 A1 | 11/2011 | Grotz et al. |
| 2012/0010653 A1 | 1/2012 | Seifert et al. |
| 2012/0029636 A1 | 2/2012 | Ragab et al. |
| 2012/0116518 A1 | 5/2012 | Grotz et al. |
| 2012/0158071 A1 | 6/2012 | Jimenez et al. |
| 2012/0185049 A1 | 7/2012 | Varela |
| 2012/0226357 A1 | 9/2012 | Varela |
| 2012/0271419 A1 | 10/2012 | Marik |
| 2012/0290094 A1 | 11/2012 | Lim et al. |
| 2012/0303124 A1 | 11/2012 | McLuen et al. |
| 2012/0323329 A1 | 12/2012 | Jimenez et al. |
| 2013/0053966 A1 | 2/2013 | Jimenez et al. |
| 2013/0144388 A1 | 6/2013 | Emery et al. |
| 2013/0158664 A1 | 6/2013 | Palmatier et al. |
| 2013/0197642 A1 | 8/2013 | Ernst |
| 2013/0317615 A1 | 11/2013 | Jimenez et al. |
| 2014/0012383 A1 | 1/2014 | Triplett et al. |
| 2014/0018924 A1 | 1/2014 | McManus et al. |
| 2014/0039622 A1 | 2/2014 | Glerum et al. |
| 2014/0088714 A1 | 3/2014 | Miller et al. |
| 2014/0140757 A1 | 5/2014 | Jimenez et al. |
| 2014/0156007 A1 | 6/2014 | Pabst et al. |
| 2014/0194991 A1 | 7/2014 | Jimenez |
| 2014/0236296 A1 | 8/2014 | Wagner et al. |
| 2014/0249629 A1 | 9/2014 | Moskowitz et al. |
| 2014/0343608 A1 | 11/2014 | Whiton et al. |
| 2015/0018951 A1 | 1/2015 | Loebl |
| 2015/0088258 A1 | 3/2015 | Jimenez et al. |
| 2015/0100128 A1 | 4/2015 | Glerum et al. |
| 2015/0148908 A1 | 5/2015 | Marino et al. |
| 2015/0272743 A1 | 10/2015 | Jimenez et al. |
| 2015/0272745 A1 | 10/2015 | Jimenez et al. |
| 2015/0272746 A1 | 10/2015 | Jimenez et al. |
| 2015/0351925 A1 | 12/2015 | Emerick et al. |
| 2016/0262907 A1 | 9/2016 | Jimenez |
| 2016/0356368 A1 | 12/2016 | Jimenez et al. |
| 2016/0377113 A1 | 12/2016 | Jimenez et al. |

FOREIGN PATENT DOCUMENTS

| | | |
|---|---|---|
| EP | 1881209 A1 | 1/2008 |
| FR | 2372998 A1 | 12/1976 |
| JP | 05-81194 | 4/1993 |
| JP | 2004-301135 A | 10/2004 |
| JP | 2008-208932 A | 9/2008 |
| WO | WO 2004/026188 A2 | 4/2004 |
| WO | WO 2004/109155 A1 | 12/2004 |
| WO | WO 2005/081330 A2 | 9/2005 |
| WO | WO 2005/096975 A2 | 10/2005 |
| WO | WO 2006/094535 A1 | 9/2006 |
| WO | WO 2006/116052 A2 | 11/2006 |
| WO | WO 2006/125329 A1 | 11/2006 |
| WO | WO 2007/002583 A2 | 1/2007 |
| WO | WO 2007/009107 A2 | 1/2007 |
| WO | WO 2007/028140 A2 | 3/2007 |
| WO | WO 2007/076377 A2 | 7/2007 |
| WO | WO 2007/111979 A2 | 10/2007 |

(56) References Cited

FOREIGN PATENT DOCUMENTS

| WO | WO 2008/137192 A1 | 11/2008 |
|---|---|---|
| WO | WO 2009/018349 A2 | 2/2009 |
| WO | WO 2010/078468 A2 | 7/2010 |
| WO | WO 2010/078520 A2 | 7/2010 |
| WO | WO 2011/011609 A2 | 1/2011 |
| WO | WO 2011/011626 A2 | 1/2011 |
| WO | WO 2014/066890 A1 | 5/2014 |

OTHER PUBLICATIONS

PCT/US2010/042915, filed Jul. 22, 2010, Search Report and Written Opinion dated Apr. 22, 2011.
PCT/US2009/069876, filed Dec. 30, 2009, International Search Report and Written Opinion dated Sep. 27, 2010, 10 pages.
PCT/US2009/069958, filed Dec. 31, 2009, International Search Report and Written Opinion dated Nov. 29, 2010, 7 pages.
PCT/US2015/055449, filed Oct. 14, 2015, International Search Report and Written Opinion dated Dec. 11, 2015, 9 pages.
PCT/US2015/032977, filed May 28, 2015, International Search Report and Written Opinion dated Sep. 21, 2015, 10 pages.
European Application No. EP 09837185, European Search Report dated May 14, 2013, 7 pages.
Japanese Application No. 2012-521784, JP Office Action dated Feb. 18, 2014, 8 pages.
PCT/US2013/067070, PCT Written Opinion/Search Report dated Feb. 27, 2014, 14 pages.
PCT/US2014/052913, PCT Written Opinion/Search Report dated Dec. 22, 2014, 10 pages.
Wenzel Spine, Inc., VariLift®-L Expandable Interbody Fusion Device: A proven solution for stand-alone fusion, Product Overview, 12 pages, 2010.
Peter A. Halverson, et. al., Tension-based Multi-stable Compliant: Rolling-contact Elements, Department of Mechanical Engineering, Brigham Young University, Provo UT, USA 84602, 34 pages, 2007.
Just L. Herder, Force Directed Design of Laparoscopic Forceps, ASME Design Engineering Technical Conference, 8 pages, 1998.
Alexander H. Slocum, Fundamentals of Design, 2005.
W. Küsswetter, A Supplementary Instrumentation for Posterior Fusion of Spine in Scoliosis, Archives of Orthopedic Traumatic Surgery, 1980, 1 page.
Chou et al., Efficacy of Anterior Cervical Fusion: Comparison of Titanium Cages, polyetheretherketone (PEEK) cages and autogenous bone grafts, Journal of Clinical Neuroscience, 2008, pp. 1240-1245.
Amelie Jeanneau, et. al., A Compliant Rolling Contact Joint and its Application in a 3-DOF Planar Parallel Mechanism with Kinematic Analysis, ASME, Design Engineering Technical Conferences, 9 pages, 2004.
Hunter et al., Overview of Medical Devices, Department of Radiology, University of Arizona, Aug. 2001, pp. 89-140, vol. 30, No. 4, ISSN: 0363-0188.
Medtronic Sofamor Danek USA, Inc., *CAPSTONE* Instrument Set Technique, http://www.mtortho.com/public/capstone.pdf , © 2005, 25 pages.
Medtronic, CAPSTONE PEEK Spinal System Surgical Technique, http://www.mtortho.com/public/capstone_peek_st.pdf, © 2009, 36 pages.
Website printout from https://seelio.com/w/fgf/omnilif-the-new-standard-in-spinal-deformity-correction-and-fusion?student=lumbarjax; dated Nov. 27, 2014, 5 pages.
Printout from Video for OmniLIF Anterior Insertion Approach from Lumber Jax; https://seelio.com/w/fgf/omnilif-the-new-standard-in-spinal-deformity-correction-and-fusion?student=lumbarjax; dated Nov. 27, 2014, 7 pages.
Printout from Video for OmniLIF Features from Lumber Jax; https://seelio.com/w/fgf/omnilif-the-new-standard-in-spinal-deformity-correction-and-fusion?student=lumbarjax; dated Nov. 27, 2014, 11 pages.
Application and File History for U.S. Appl. No. 12/407,608, filed Mar. 19, 2009, Inventors Jimenez et al.
Application and File History for U.S. Appl. No. 12/650,994, filed Dec. 31, 2009, Inventors Jimenez et al.
Application and File History for U.S. Appl. No. 12/651,266, filed Dec. 31, 2009, Inventors Jimenez et al.
Application and File History for U.S. Appl. No. 12/841,465, filed Jul. 22, 2010, now U.S. Pat. No. 8,303,663, Inventors Jimenez et al.
Application and File History for U.S. Appl. No. 12/841,869, filed Jul. 22, 2010, Inventors Jimenez et al.
Application and File History for U.S. Appl. No. 13/189,410, filed Jul. 22, 2011, Inventor Jimenez.
Application and File History for U.S. Appl. No. 13/661,534, filed Oct. 26, 2012, Inventor Jimenez.
Application and File History for U.S. Appl. No. 13/591,463, filed Aug. 22, 2012, Inventor Jimenez.
Application and File History for U.S. Appl. No. 13/891,356, filed May 10, 2013, Inventor Jimenez et al.
Application and File History for U.S. Appl. No. 14/024,764, filed Sep. 12, 2013, Inventor Jimenez et al.
Application and File History for U.S. Appl. No. 14/563,660, filed Dec. 8, 2014. Inventor Jimenez et al.
Application and File History for U.S. Appl. No. 14/242,451, filed Apr. 1, 2014. Inventor Jimenez et al.
Application and File History for U.S. Appl. No. 14/318,196, filed Jun. 27, 2014. Inventor Jimenez et al.
Application and File History for U.S. Appl. No. 14/592,507, filed Jan. 8, 2015. Inventor Jimenez et al.
Application and File History for U.S. Appl. No. 14/585,544, filed Dec. 30, 2014. Inventor Jimenez et al.
Application and File history for U.S. Appl. No. 15/164,498, filed May 25, 2016. Inventors: Jimenez et al.
European Application No. EP 10802916.6, Examination Report dated May 12, 2016, 4 pages.
Canadian Application No. 2,768,867 Office Action dated Aug. 4, 2016, 4 pages.
Canadian Application No. 2,768,867, Office Action dated Apr. 19, 2017, 4 pages.
Application and File history for U.S. Appl. No. 15/174,454, filed Jun. 6, 2016, Inventors: Jimenez et al.
Application and File history for U.S. Appl. No. 15/332,066, filed Oct. 24, 2016. Inventors: Jimenez et al.
Application and File history for U.S. Appl. No. 15/198,557, filed Jun. 30, 2016. Inventors: Jimenez et al.
Application and File history for U.S. Appl. No. 15/591 214, filed May 10, 2017. Inventors: Jimenez et al.

* cited by examiner

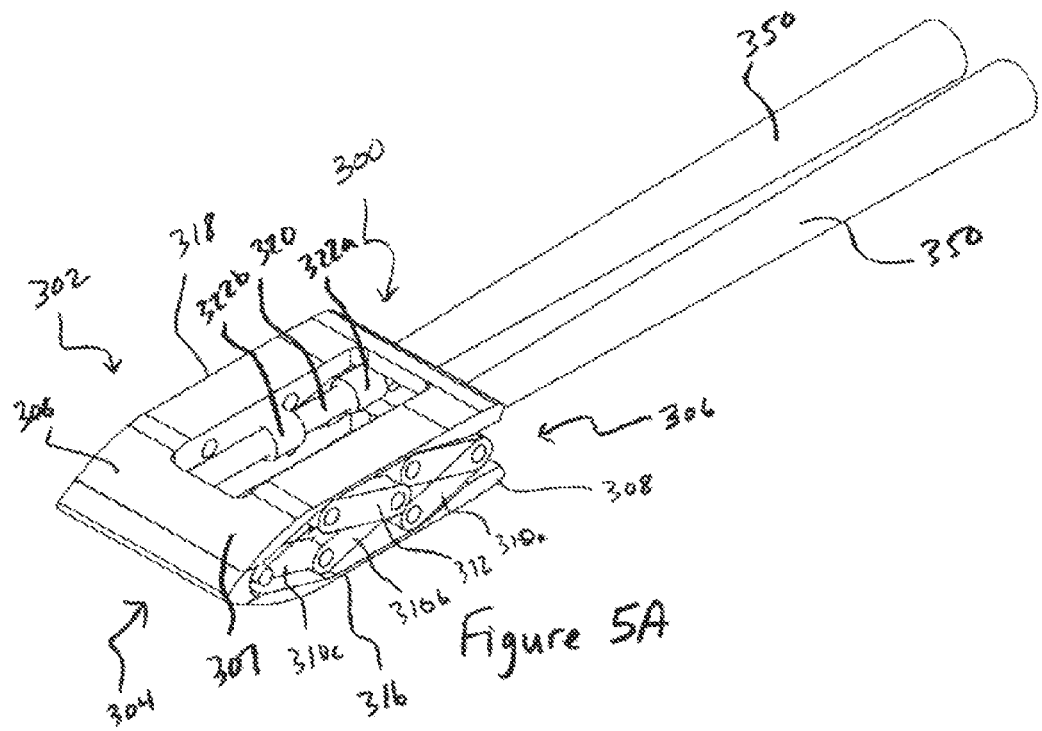
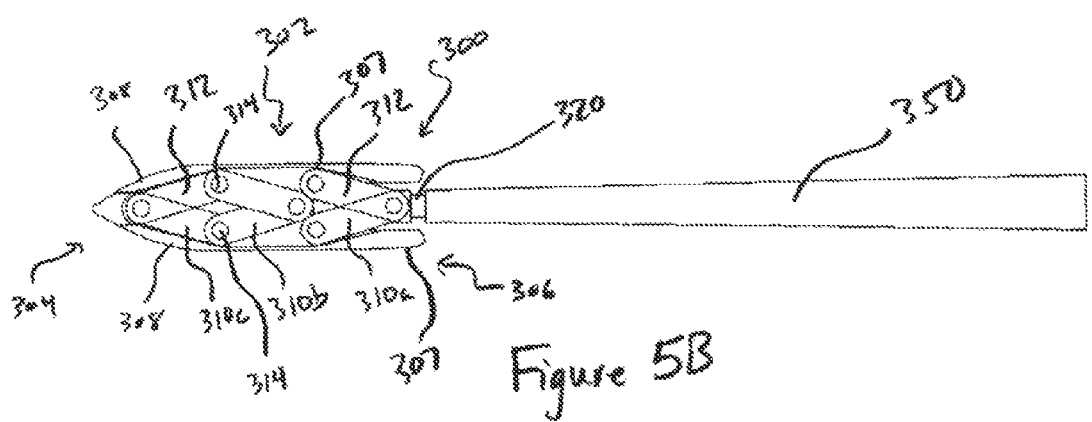

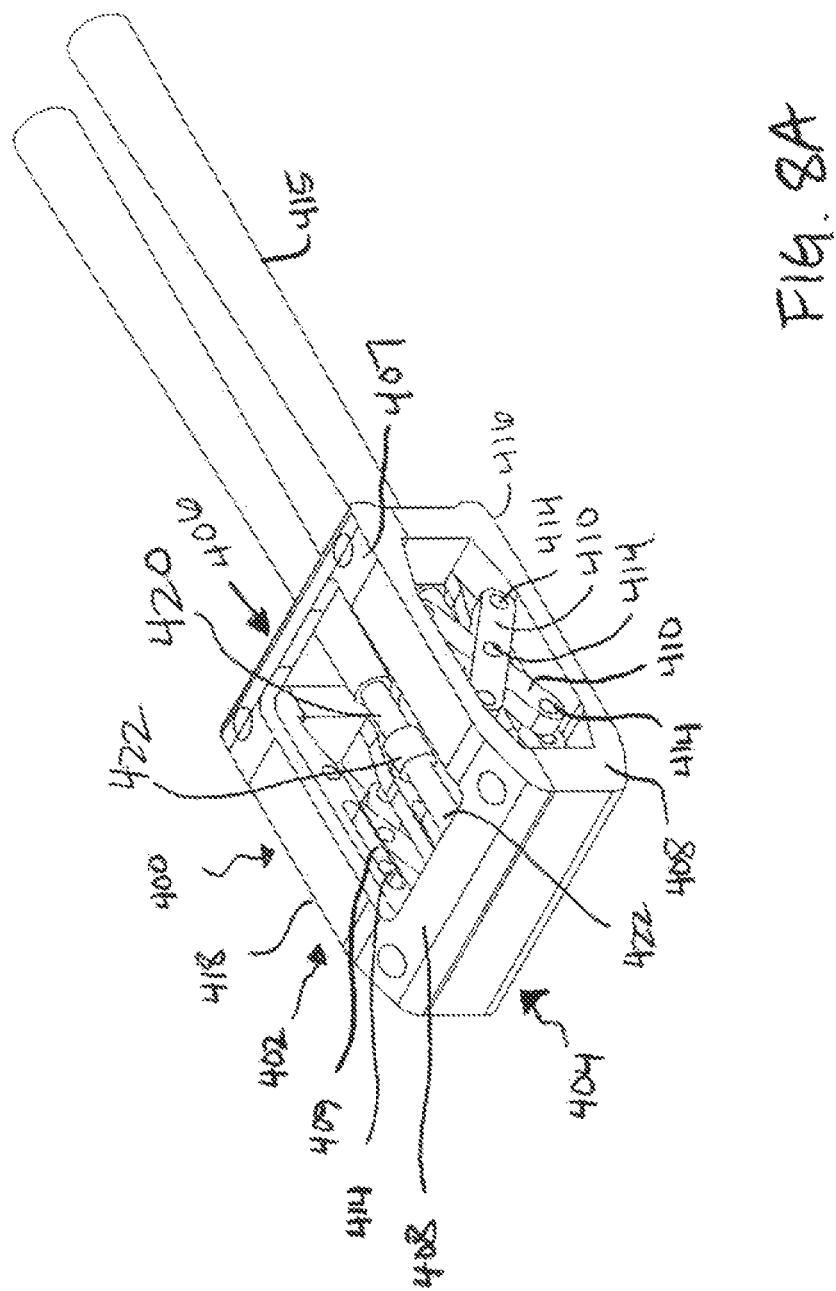

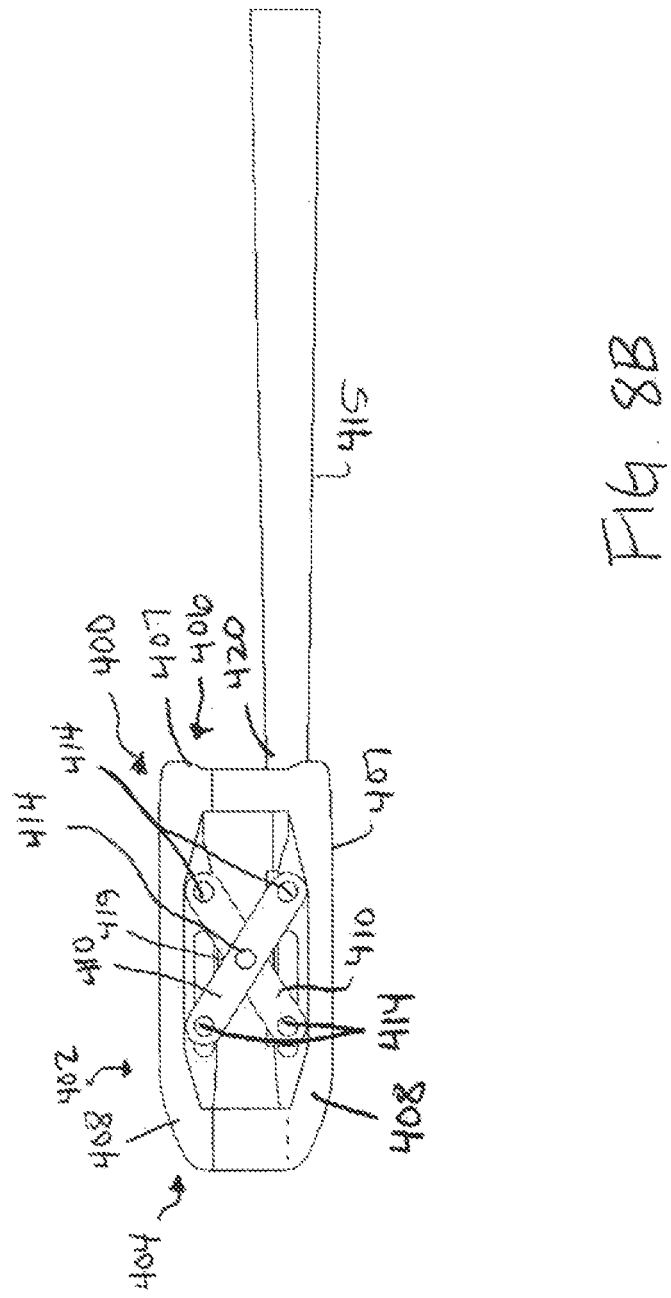

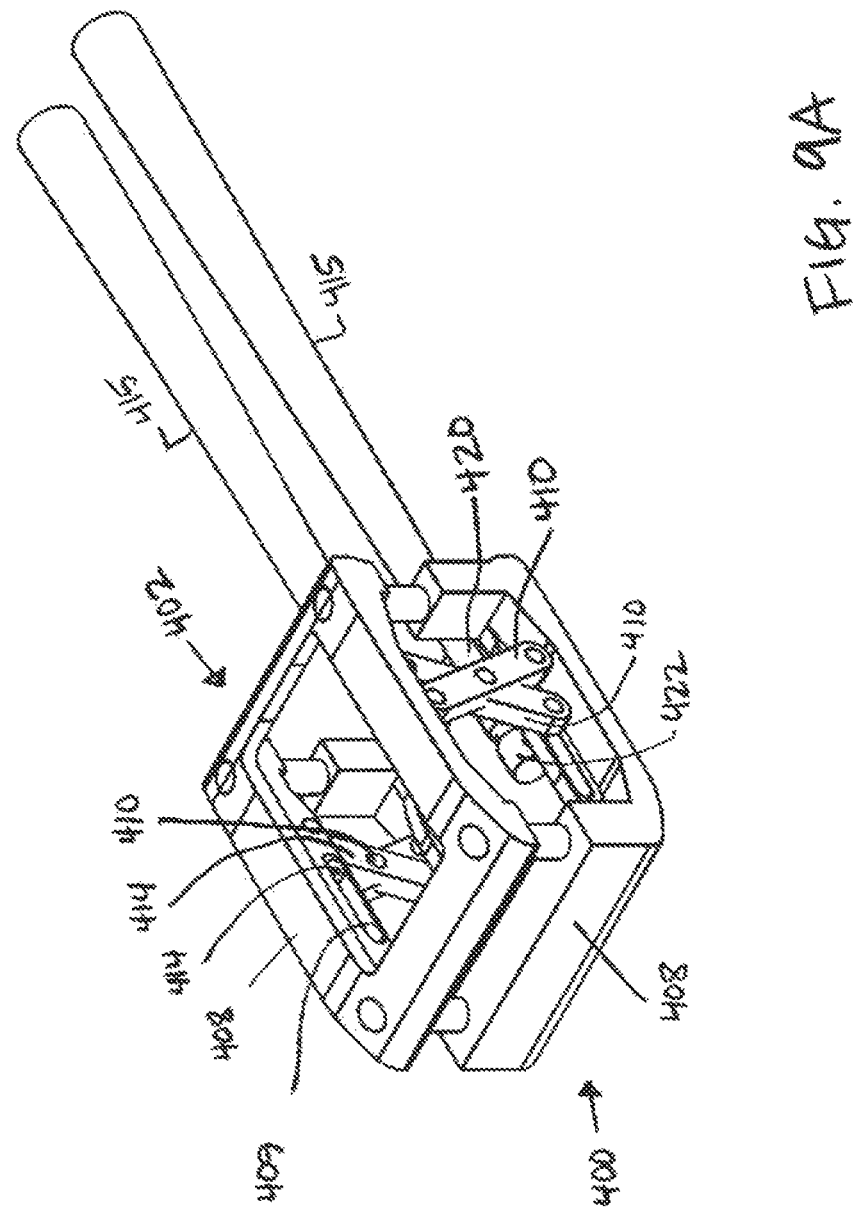

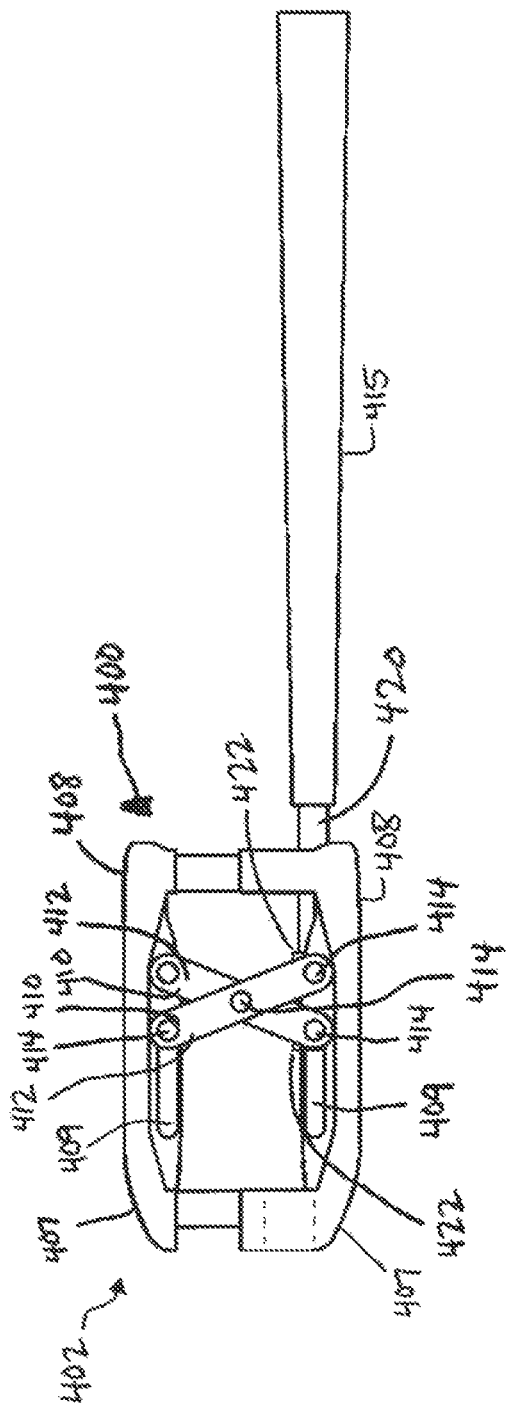

STABLE DEVICE FOR INTERVERTEBRAL DISTRACTION AND FUSION

RELATED APPLICATION

This application is a continuation of U.S. application Ser. No. 12/407,608, filed Mar. 19, 2009, now U.S. Pat. No. 8,628,577, which is related to U.S. Provisional Application No. 61/038,039, filed Mar. 19, 2008, and U.S. application Ser. No. 12/118,767, filed May 12, 2008, each of which is hereby fully incorporated herein by reference.

FIELD OF THE INVENTION

The present invention relates to the distraction and fusion of vertebral bodies. More specifically, the present invention relates to devices and associated methods for distraction and fusion of vertebral bodies that remain stable when implanted and facilitate fusion following their use for distraction. In addition, the present invention aids in the correction of spinal deformity by reducing a collapse disc and establishing sagittal alignment, lordosis or kyphosis.

BACKGROUND OF THE INVENTION

The concept of intervertebral fusion for the cervical and lumbar spine following a discectomy was generally introduced in the 1960s. It involved coring out a bone graft from the hip and implanting the graft into the disc space. The disc space was prepared by coring out the space to match the implant. The advantages of this concept were that it provided a large surface area of bone to bone contact and placed the graft under loading forces that allowed osteoconduction and induction enhancing bone fusion. However, the technique is seldom practiced today due to numerous disadvantages including lengthy operation time, destruction of a large portion of the disc space, high risk of nerve injury, and hip pain after harvesting the bone graft.

Presently, at least two devices are commonly used to perform the intervertebral portion of an intervertebral body fusion: the first is the distraction device and the second is the intervertebral body fusion device, often referred to as a cage. Cages can be implanted as standalone devices or as part of a circumferential fusion approach with pedicle screws and rods. The concept is to introduce an implant that will distract a collapsed disc and decompress the nerve root, allow load sharing to enhance bone formation and to implant a device that is small enough to allow implantation with minimal retraction and pulling on nerves.

In a typical intervertebral body fusion procedure, a portion of the intervertebral disc is first removed from between the vertebral bodies. This can be done through either a direct open approach or a minimally invasive approach. Disc shavers, pituitary rongeours, curettes, and/or disc scrapers can be used to remove the nucleus and a portion of either the anterior or posterior annulus to allow implantation and access to the inner disc space. The distraction device is inserted into the cleared space to enlarge the disc space and the vertebral bodies are separated by actuating the distraction device. Enlarging the disc space is important because it also opens the foramen where the nerve root exists. It is important that during the distraction process one does not over-distract the facet joints. An intervertebral fusion device is next inserted into the distracted space and bone growth factor, such as autograft, a collagen sponge with bone morphogenetic protein, or other bone enhancing substance may be inserted into the space within the intervertebral fusion device to promote the fusion of the vertebral bodies.

Intervertebral fusion and distraction can be performed through anterior, posterior, oblique, and lateral approaches. Each approach has its own anatomic challenges, but the general concept is to fuse adjacent vertebra in the cervical thoracic or lumbar spine. Devices have been made from various materials. Such materials include cadaveric cancellous bone, carbon fiber, titanium, and polyetheretherketone (PEEK). Devices have also been made into different shapes such as a bean shape, football shape, banana shape, wedge shape, and a threaded cylindrical cage.

U.S. Pat. Nos. 7,070,598 and 7,087,055 to Lim et al. disclose minimally invasive devices for distracting the disc space. The devices include scissor-jack-like linkages that are used to distract a pair of endplates associated with adjacent vertebra from a first collapsed orientation to a second expanded orientation. A pull arm device is used to deliver and distract the device in the disc space. However, the device is primarily used for distraction and not subsequent vertebral fusion. The device would not work as a fusion device, because once the pull arm is disconnected from the device, the device will not be stable enough to maintain proper spacing of the vertebrae until fusion can occur. The endplates of the device are also solid and do not permit bone growth for successful fusion.

U.S. Patent Publication No. 2008/0114367 to Meyer discloses a device that uses a scissor-jack-like arrangement to distract a disc space. To solve the instability problem of the scissor-jack arrangement, a curable polymer is injected to fill the disc space and the distraction device is disabled from attempting to support the load. The curable polymer and disabling of the device are necessary because the device could not adequately support the distracted disc space. The base plates of the device have at least two or more degrees of freedom, collectively, in a distracted position and are therefore not stable under the loads encountered supporting the disc space. Absent injection of the polymer, and the support and control supplied by the implanting physician via the removable distraction tool, the base plates would collapse, which could cause severe damage to the vertebral bodies.

Accordingly, there is a need in the art for a device that can distract adjacent vertebral bodies in a minimally invasive manner while providing stable support for the disc space during fusion.

SUMMARY OF THE INVENTION

Improved methods and apparatuses for vertebral body distraction and fusion in accordance with various embodiments of the present invention employ a means for stabilizing a device so that it can stay in the body and stably support the disc space during vertebral fusion following its use as a distraction device. The device is expected to be capable of supporting prolonged, compressive loading of greater than 2000-3000 [N]; oblique shear loading of greater than 1200-1500 [N]; and torsion of greater than 10-20 [N]. The device is inserted into the disc space and distracted from a compressed configuration to an expanded configuration to distract the disc space. Mechanisms for stabilizing constrains of the device to zero, or fewer, degrees of freedom of movement enables the device to stably support the disc space. A bone growth stimulant for promoting vertebral fusion can be inserted into an open space defined by the device, which continues to stably support the disc space during vertebral fusion.

In one embodiment, a device can be used for both intervertebral distraction and fusion of an intervertebral disc space. The device can include a top base plate having a top bearing surface configured to interface with an end plate of a superior vertebra of the intervertebral disc space and a bottom base plate having a bottom bearing surface configured to interface with an end plate of an inferior vertebra of the intervertebral disc space. A first arm and a second arm can each be hinged and connected to the top base plate and the bottom base plate. A threaded member can extend through the first arm and into the second arm and be configured such that rotation of the threaded member in a first direction causes expansion of the first and second arms such that the top bearing surface and bottom bearing surface move away from each other into a distracted position. The device also includes a means for stabilizing the top base plate and bottom base plate such that the device has zero degrees of freedom of movement in the distracted position and is designed to remain in the body and stably maintain the intervertebral disc space during vertebral fusion following being moved to the distracted position.

Optionally, some flexibility or compliance may be built into the device, while maintaining the stability of the device, by selecting flexible materials for some of the rigid members and or by manipulating the fits of the numerous joints. Flexible material may also be added to, in, around, or between elements of the device to additionally support flexibility, while maintaining, or in some embodiments, enhancing, the stability of the device by reducing potential hysteresis.

In another embodiment, a method of intervertebral body distraction and fusion involves implantation of a distractible intervertebral body fusion device into an intervertebral disc space. The device is inserted such that a top bearing surface of a top base plate of the device interfaces with an end plate of a superior vertebra of the disc space and a bottom bearing surface of a bottom base plate interfaces with an end plate of an inferior vertebra of the disc space. The device is distracted into an expanded configuration such that the top base plate and bottom base plate are vertically separated from each other to expand the disc space. A bone growth promoting material can then be inserted into the disc space into an open space defined by the device to encourage bone growth and fusion through one or more openings in the base plates. The bone growth promoting material can then be allowed to aid in intervertebral fusion of the adjacent vertebrae while the device stably supports the vertebrae with zero degrees of freedom of movement.

The above summary of the various embodiments of the invention is not intended to describe each illustrated embodiment or every implementation of the invention. This summary represents a simplified overview of certain aspects of the invention to facilitate a basic understanding of the invention and is not intended to identify key or critical elements of the invention or delineate the scope of the invention.

BRIEF DESCRIPTION OF THE DRAWINGS

The invention may be more completely understood in consideration of the following detailed description of various embodiments of the invention in connection with the accompanying drawings, in which:

FIG. 5A is a perspective view of a distractible intervertebral body fusion device according to an aspect of the present invention.

FIG. 5B is a side view of the distractible intervertebral body fusion device of FIG. 5A.

FIG. 8A is a perspective view of a distractible intervertebral body fusion device according to an aspect of the present invention.

FIG. 8B is a side view of the distractible intervertebral body fusion device of FIG. 8A.

FIG. 9A is a perspective view of the distractible intervertebral body fusion device of FIG. 8A in an expanded configuration.

FIG. 9B is a side view of the distractible intervertebral body fusion device of FIG. 8A in an expanded configuration.

Figure 1A:
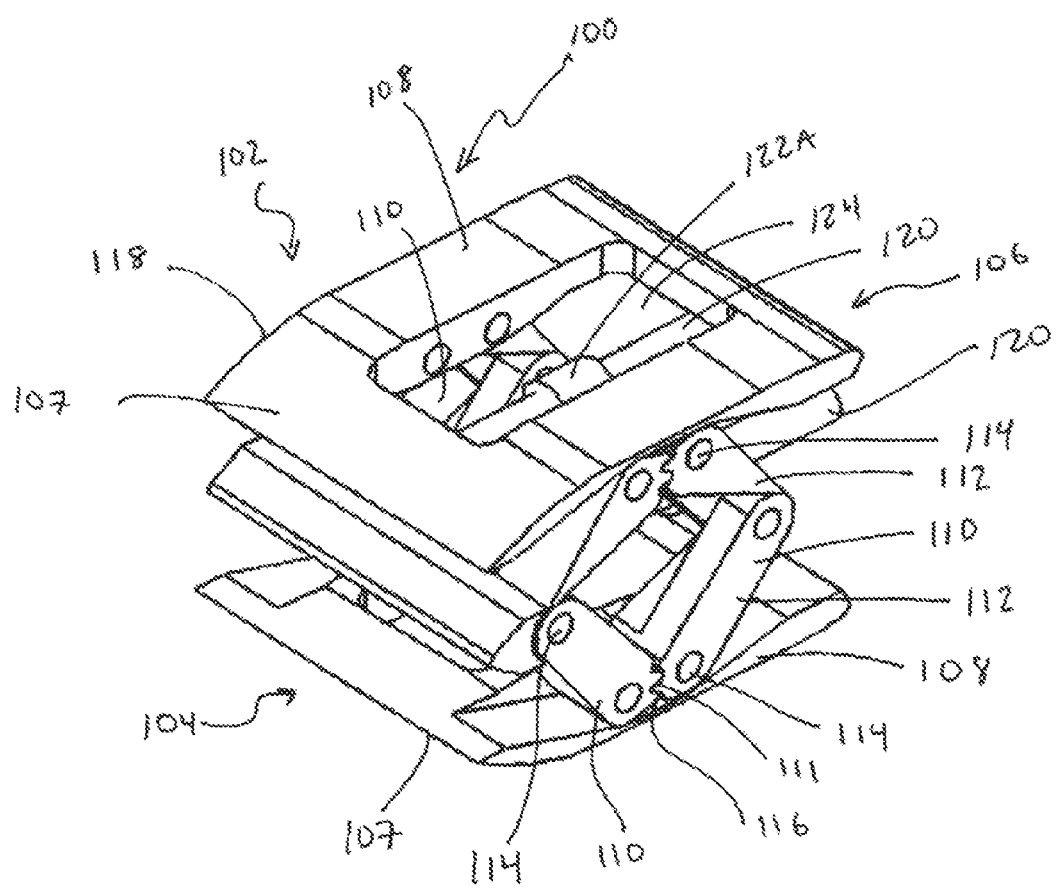
FIG. 1A is a perspective view of an embodiment of a distractible intervertebral body fusion device according to an aspect of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE DRAWINGS

In the following detailed description of the present invention, numerous specific details are set forth in order to provide a thorough understanding of the present invention. However, one skilled in the art will recognize that the present invention may be practiced without these specific details. In other instances, well-known methods, procedures, and components have not been described in detail so as to not unnecessarily obscure aspects of the present invention.

Figure 1B:
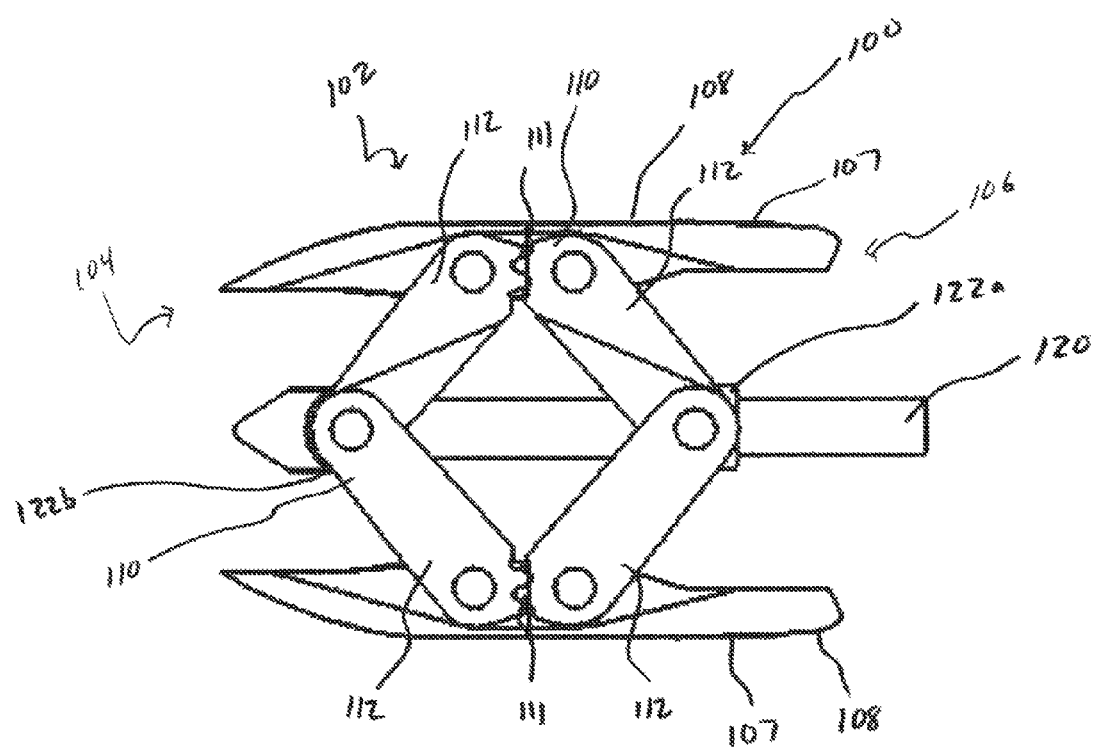
FIG. 1B is a side view of the distractible intervertebral body fusion device of FIG. 1A.
Figure 1C:
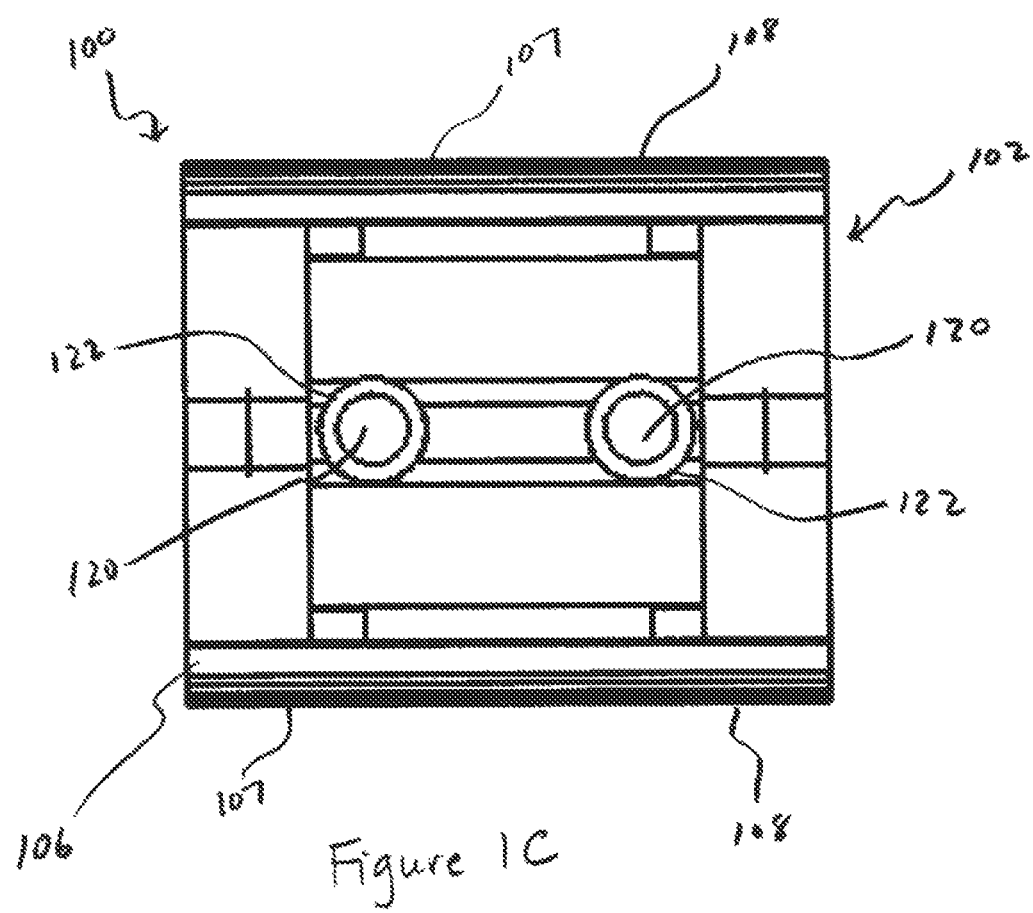
FIG. 1C is an end view of the distractible intervertebral body fusion device of FIG. 1A.
Figure 1D:
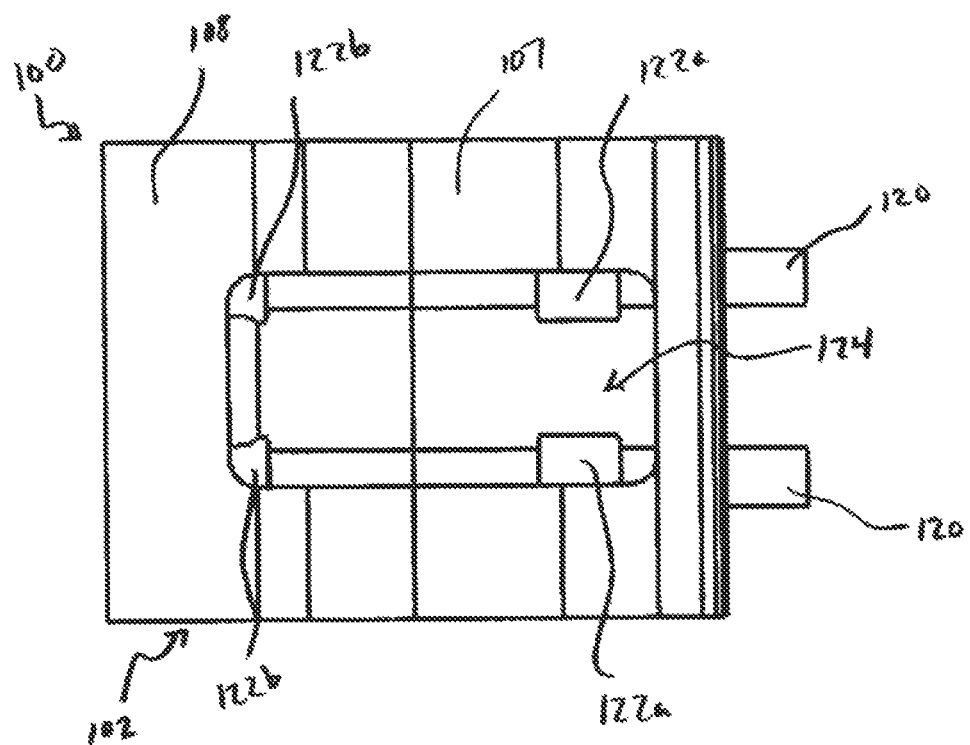
FIG. 1D is a top view of the distractible intervertebral body fusion device of FIG. 1A.

Referring to FIGS. 1A-1C, there can be seen a distractible intervertebral body fusion device 100 according to an aspect of the present invention. Device 100 includes a device body 102. Device body 102 can include a nose portion 104, a rear portion 106, a pair of opposed base plates 108 having outer bearing surfaces 107, and arms 110. As used throughout this disclosure, "bearing surface" refers to the outside surface of a base plate that interfaces with the endplate of a vertebra. Each arm 110 can include a pair of structural members 112 hingedly attached to each other, with each structural member 112 hingedly attached to one of the base plates 108. In one embodiment, structural members 112 are hinged to each other and to base plates 108 with pins 114. Structural members 112 on opposing arms 110 can interlock with each other via gear teeth 111 positioned on the ends of structural members 112. Gear teeth 111 are arranged so as to keep the device 100 stable when it is distracted within the body and supporting a load. In one embodiment, device 100 includes a pair of arms 110 on a first side 116 and a pair of arms 110 on a second side 118 of device 100.

Threaded members 120, such as screws, can be inserted through blocks 122a attached to the arm 110 nearest the rear portion 106 and into blocks 122b attached to the arm 110 nearest the nose portion 104. Actuation of threaded members 120 in a first direction drives blocks 122 closer together, which causes expansion of arms 110 and distraction of base plates 108. Actuation of threaded members 120 in the opposite direction would drive blocks 122 apart, thereby bringing base plates 108 closer together. This back-drivability of the device 100 is helpful for sizing the device 100 and removing the device 100 if necessary, such as in the event of post-surgical infection or trauma. Portions of the threaded members 120 may be reverse threaded to allow distraction without changing the position of the threaded members along the respective axes of the threaded members helping to keep the device from adversely interacting with the anatomy of the patient. In one embodiment, blocks 122a can be tapped to accommodate threaded members 120 and blocks 122b can provide a clearance fit with threaded members 120. When threaded members 120 are actuated, this allows blocks 122b to be pulled towards blocks 122a, causing the device 100 to distract. Alternatively, instead of threaded members 120 extending through a separate block portion 122 of arms 110 connected to structural members 112, threaded members 120 can extend through apertures directly through structural members 112.

In one embodiment, each base plate 108 includes an opening 124 to facilitate bone growth through the device 100. Openings 124 promote vertebral fusion because bone can grow directly through the device 100. Although depicted as being generally rectangular, opening 124 can comprise any shape. Alternatively, a generally solid surface or a surface with multiple openings can be provided on each base plate 108. Endplates 108 can also have a rough surface or teeth to create friction with the base plates of the vertebra to prevent accidental extrusion of the device 100 or to promote bone growth for successful fusion. Nose portion 104 can be tapered to facilitate insertion of the device 100 into the disc space. Rear portion 106 can also be tapered.

In various embodiments, device body 102 is shaped to be ergonomic. Device body 102 can have various shapes, such as, for example, rectangular or kidney-shaped. A kidney-shaped device body 102 maximizes contact between the device and the vertebral bodies because the base plates of vertebrae tend to be slightly concave. One or both ends of the device may also be tapered to facilitate insertion. This minimizes the amount of force needed to initially separate the vertebral bodies. In addition, the device may be convex along both its length and its width, or bi-convex. Device body can also be comprised of various materials. Such materials can include, for example, titanium, steel, PEEK and carbon fiber. Device can also be constructed in various sizes depending on the type of vertebra and size of patient with which it is being used. In some embodiments, the threaded member 120 can be micro-machined, or split along its length and reconnected using a bellows or flexible torque transmission device, to be able to operate through an angle that may be necessitated by the shape of the device.

Figure 2A:
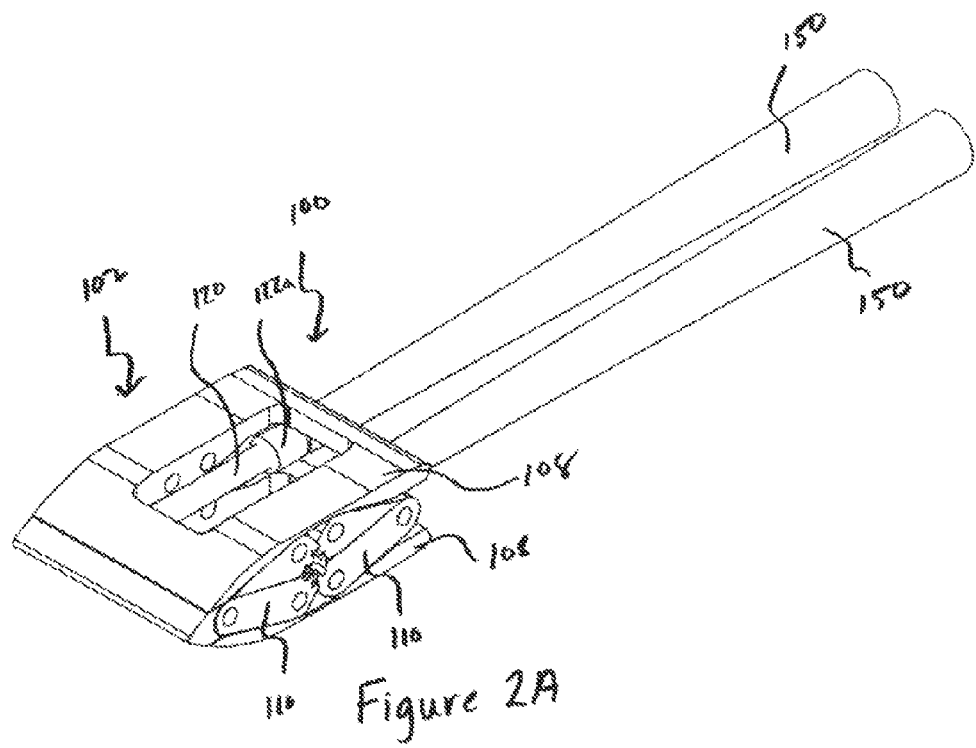
FIG. 2A is a perspective view of the distractible intervertebral body fusion device of FIG. 1A in a compressed configuration.
Figure 2B:
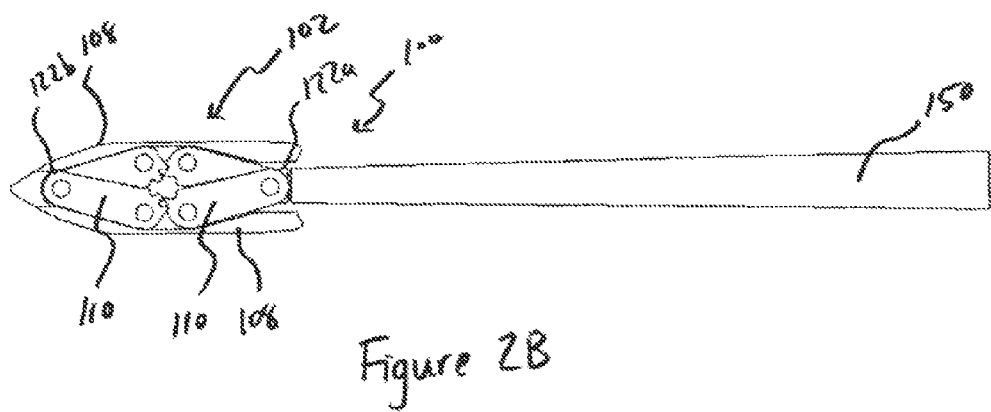
FIG. 2B is a side view of the distractible intervertebral body fusion device of FIG. 1A in a compressed configuration.
Figure 3A:
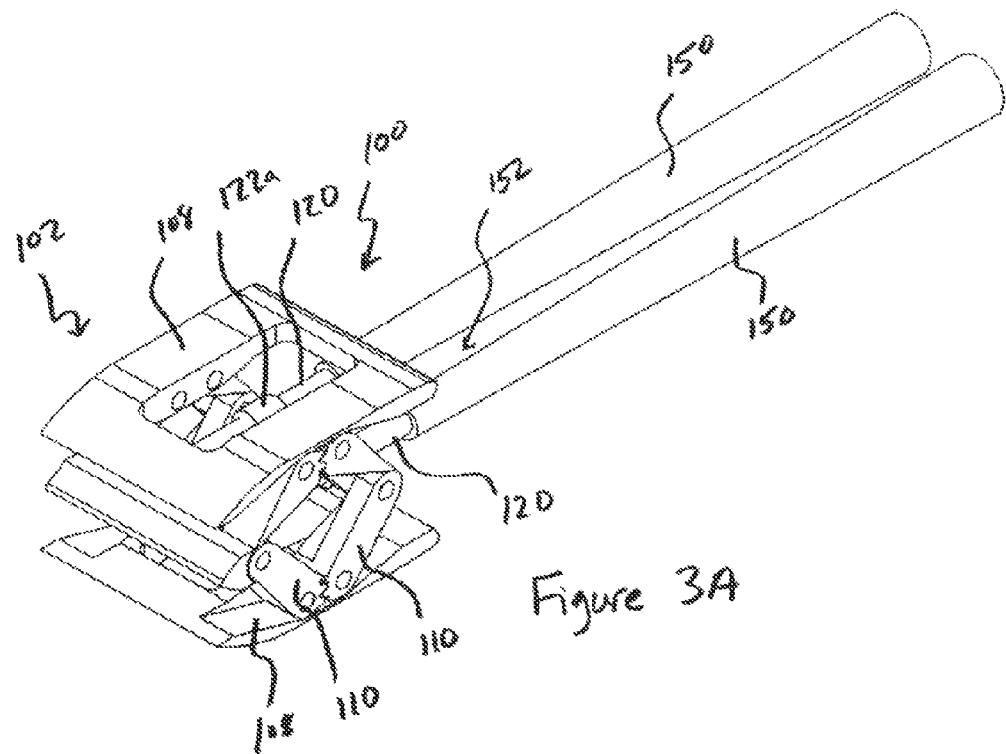
FIG. 3A is a perspective view of the distractible intervertebral body fusion device of FIG. 1A in an expanded configuration.
Figure 3B:
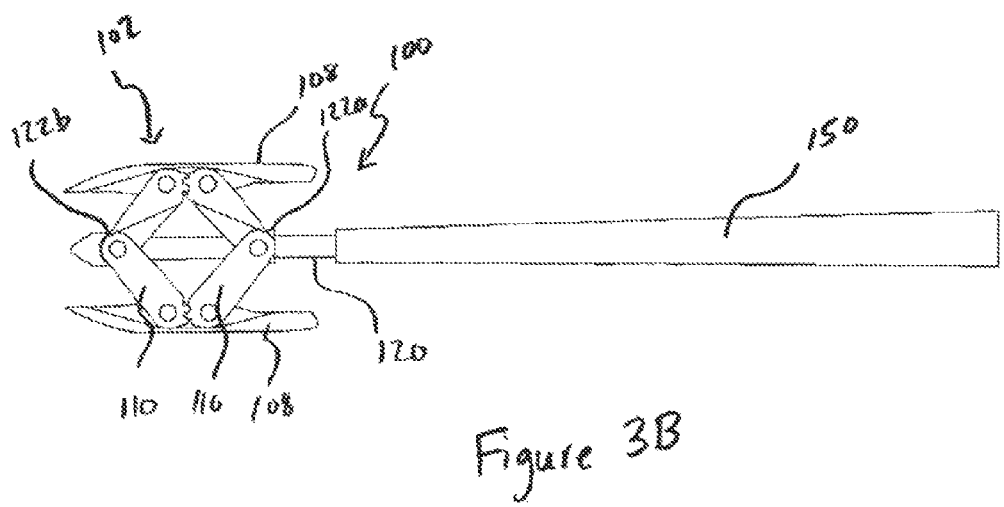
FIG. 3B is a side view of the distractible intervertebral body fusion device of FIG. 1A in an expanded configuration.

Device 100 can be placed between adjacent vertebrae or vertebral bodies and used to distract the endplates of the adjacent vertebral bodies and subsequently serve as a fusion device. One or more insertion tools 150 can be used to insert and distract device 100. Referring to FIGS. 2A and 2B, the device body 102 can be seen in its initial compressed configuration. In FIGS. 3A and 3B, device body 102 is in an expanded configuration. Insertion tools 150 can be connected to threaded members 120 and first used to insert device 100 into a desired location. Device 100 can be inserted with tapered nose portion 104 first. One device 100 can be inserted, or, for additional support, two devices 100 can be inserted. Two devices 100, each sized to be inserted within one-half of the evacuated disc space, can be especially useful for treating larger patients in which the device may encounter higher loads. In another embodiment, three or more small devices can be inserted into the disc space in order to very accurately control the orientation and distance between the discs. Three or more distraction mechanisms may be positioned circumferentially between two circular endplates to result in very accurate control and orientation of the base plates. Such a device would resemble a hexapod.

To distract device 100, insertion tools 150 can be used to rotate threaded members 120 in a first direction. This causes blocks 122b to be pulled towards blocks 122a, which causes arms 110 to expand and base plates 108 to distract. Threaded members 120 can be actuated the same amount (either simultaneously or independently) for uniform distraction or can be actuated different amounts for non-uniform distraction with one side 116 or 118 of the device higher than the other. The endplates 108 or other elements of the device 100 may in some embodiments be made compliant for exaggerated non-uniform distraction while maintaining the stability of the device 100. Once base plates 108 are distracted to a desired degree, insertion tools can be disconnected from threaded members 120 and the device 100 can remain within the body. In one embodiment, a locking mechanism can be utilized to prevent rotation of the threaded members to ensure the device remains in the distracted state. In one embodiment, the locking mechanism can be activated with the insertion device. In one embodiment, locking may be enhanced by tightening a threaded nut (not shown) against one or more of the threaded blocks 122.

Figure 12:
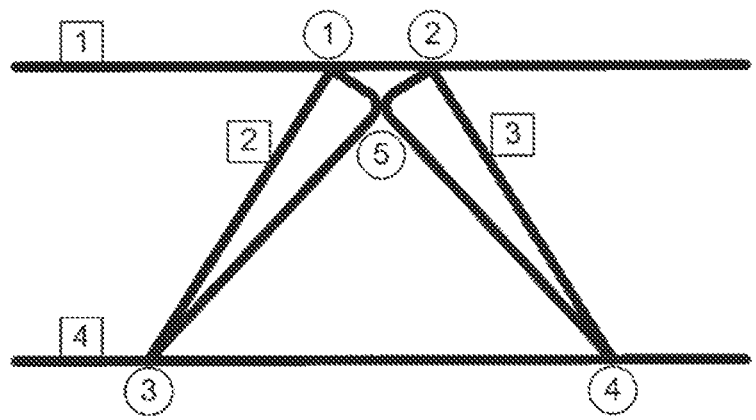
FIG. 12 is a simplified of a distractible intervertebral body fusion device according to an aspect of the present invention.

Device 100 is capable of stably supporting the vertebral bodies in the distracted position. Interlocked gear teeth 111 of structural members 112 in addition to threaded members 120 interlocked with blocks 122 constrain the device such that there are zero, or fewer, degrees of freedom. A typical four bar planar linkage has four links and has four kinematic pairs each limiting two degrees of freedom and each allowing one degree freedom resulting in the four bar planar linkage having one degree of freedom overall. Gears such as those of gear teeth 111 may be added as described above to create one additional kinematic pair limiting the device in one or more additional degree(s) of freedom thus resulting in an overall freedom of zero or fewer degrees of freedom. That is, none of the linkages that comprise the device are capable of independent movement with respect to the other linkages. According to Gruebler's equation the number of degrees of freedom of a planar linkage=$3*(n-1)-2f$, where n is the number of links in the linkage and f is the number of one degree of freedom kinematic pairs in the linkage. Referring to FIG. 12, a simplified view of a distractible intervertebral body fusion device can represent device 100, where the symbol (5) represents the gear teeth. Without the gear teeth, the device has four links and four kinematic pairs and therefore $3*(4-1)-2*4=1$ degree of freedom. The device would therefore be unstable when supporting a load. Adding in the gear teeth, however, adds a kinematic coupling and there are therefore $3*(4-1)-2*5=-1$ degrees of freedom. The device is therefore actually over constrained (meaning that there are additional constraints beyond the minimum necessary to make it stable), and stable under loading conditions. This allows device 100 to stably support the disc space upon distraction. In some embodiments, a crush surface or compliant materials may be used in concert with or in place of the interlocking gear teeth 111 or hinges 114 to minimize hysteresis that may be present in the device 100 and due to clearance in the gear teeth 111 and hinge mechanisms 114 necessary for overcoming the over-constraint in devices having fewer than zero degrees of freedom.

Once device is inserted and supporting the adjacent vertebral bodies, it can be utilized to promote vertebral fusion. Following distraction, a bone growth stimulant, such as autograft, bone morphogenic protein, or bone enhancing material, can be delivered into an open area defined within the device. In one embodiment, bone growth stimulant is delivered after insertion tools 150 are disconnected. In another embodiment, bone growth stimulant is delivered through an open area between insertion tools 150. In a further embodiment, bone growth stimulant can be delivered by the insertion tools 150 through a hollow chamber within insertion tools 150. Device is then capable of supporting in-vivo loads during the 6 to 12 weeks that fusion occurs between the vertebral bodies. In one embodiment, openings 124 in base plates 108 promote and allow for bone growth into and through the device 100.

Figure 4A:
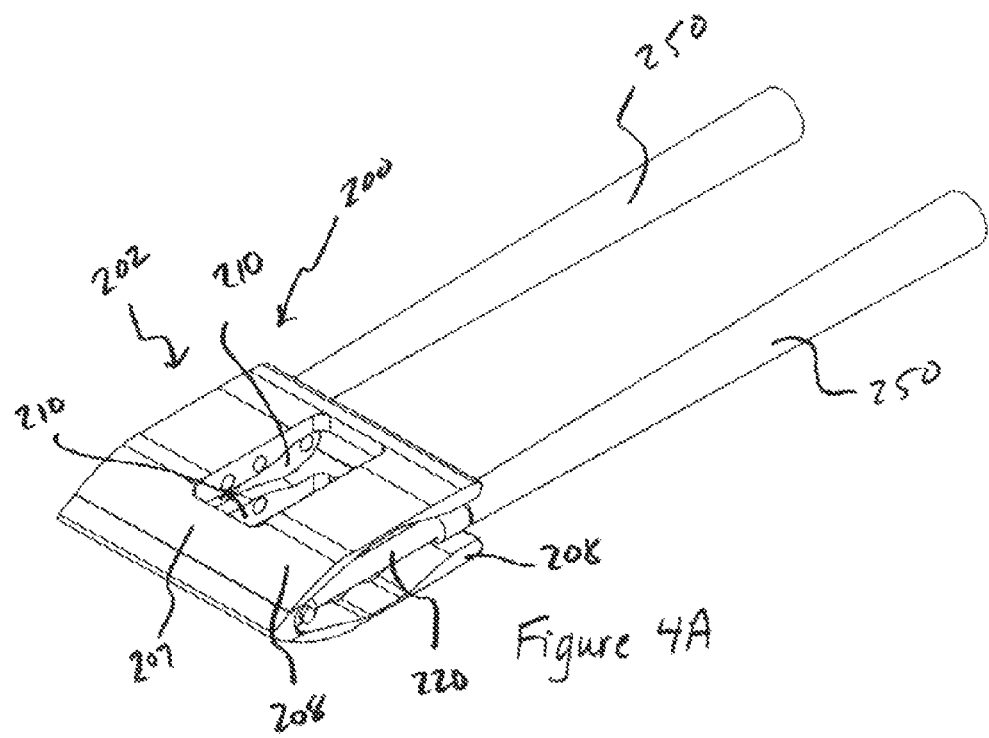
FIG. 4A is a perspective view of an embodiment of a distractible intervertebral body fusion device according to an aspect of the present invention.
Figure 4B:
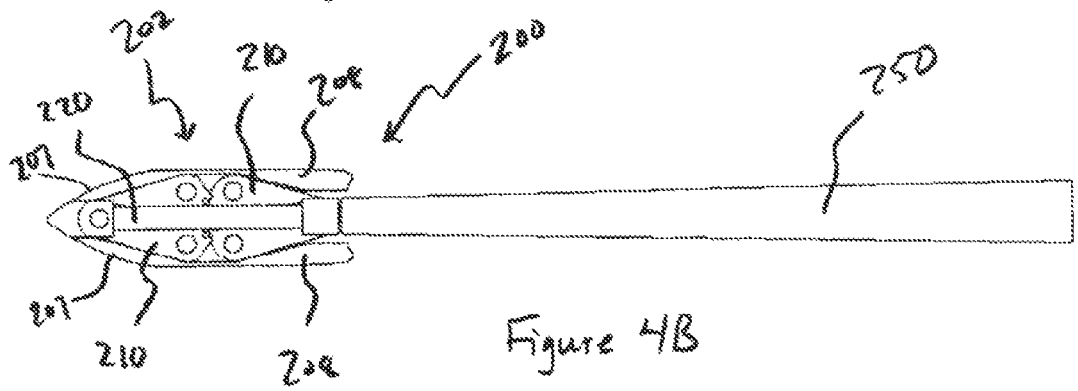
FIG. 4B is a side view of the distractible intervertebral body fusion device of FIG. 4A.
Figure 4C:
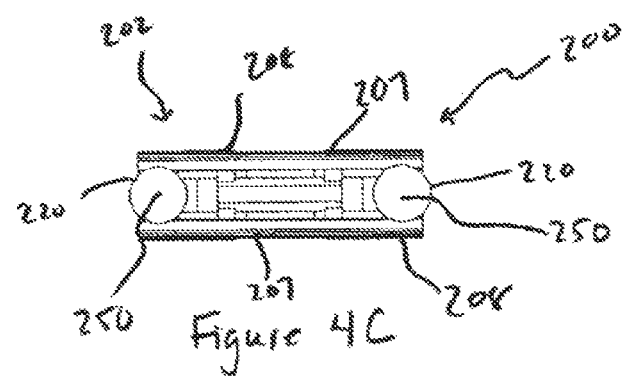
FIG. 4C is an end view of the distractible intervertebral body fusion device of FIG. 4A.

Referring now to FIGS. 4A-4C, there can be seen another embodiment of a distractible intervertebral fusion device 200 according to an aspect of the present invention. This embodiment of the device 200 similarly includes a device body 202 having a pair of opposed base plates 208 with outer bearing surfaces 207 connected with arms 210 that are distractible with threaded members 220. In this embodiment, threaded members 220 are positioned outside of arms 210, as opposed to device 100, where the threaded members 120 are positioned inside of the arms 110. This provides for additional space between insertion tools 250 and threaded members 220 for delivering bone growth stimulant to aid in vertebral fusion following distraction. Additionally the external location of the screws may enhance the ability of the device to carry torsional loading the device may experience during implantation or fusion.

Referring now to FIGS. 5A-5B and 6A-6B, there can be seen a further embodiment of a distractible intervertebral fusion device 300 according to an aspect of the present invention. Device 300 includes a device body 302 including a nose portion 304, a rear portion 306, a pair of opposed base plates 308 with outer bearing surfaces 307, and arms 310. Each arm 310 includes a pair of structural members 312 hingedly attached to each other and to one of the base plates 308. In one embodiment, structural members 312 are hinged to each other and to base plates 308 with pins 314. Device 300 can have arms 310 on both side 316, 318 of device 300.

Figure 7:
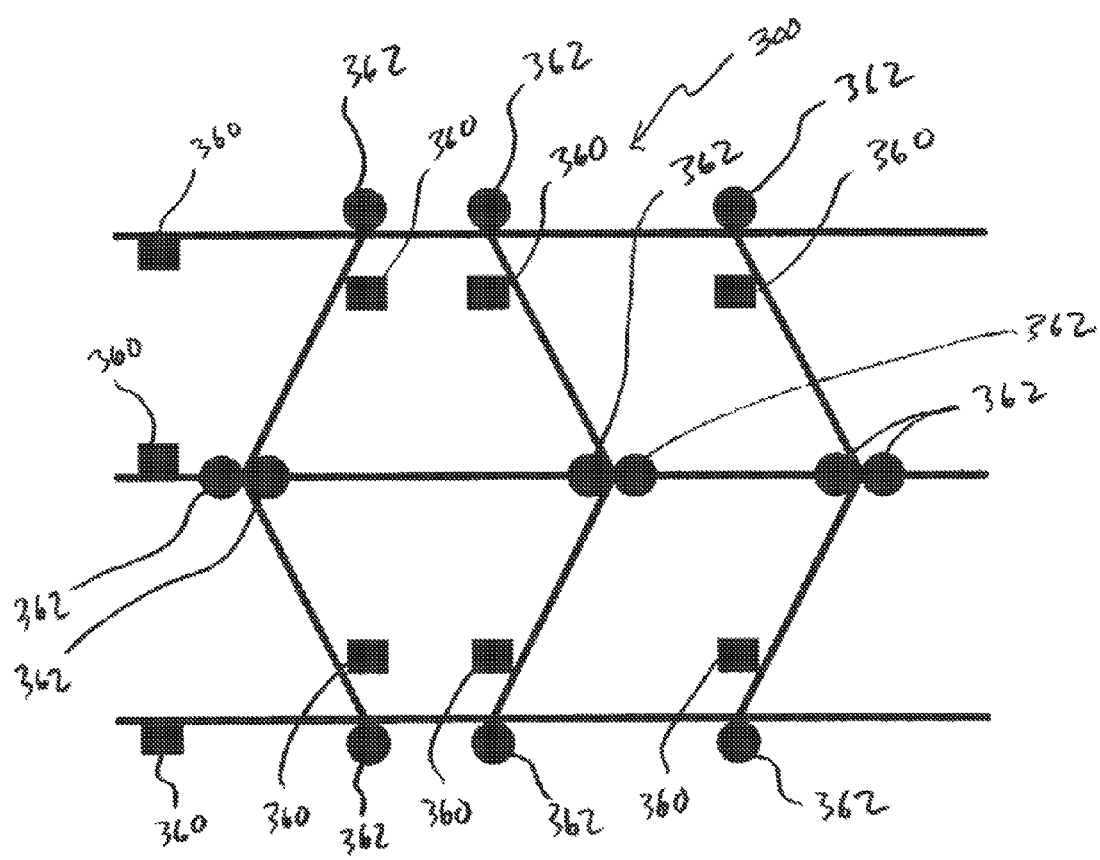
FIG. 7 is a simplified view of the distractible intervertebral body fusion device of FIG. 5A.
Figure 10A:
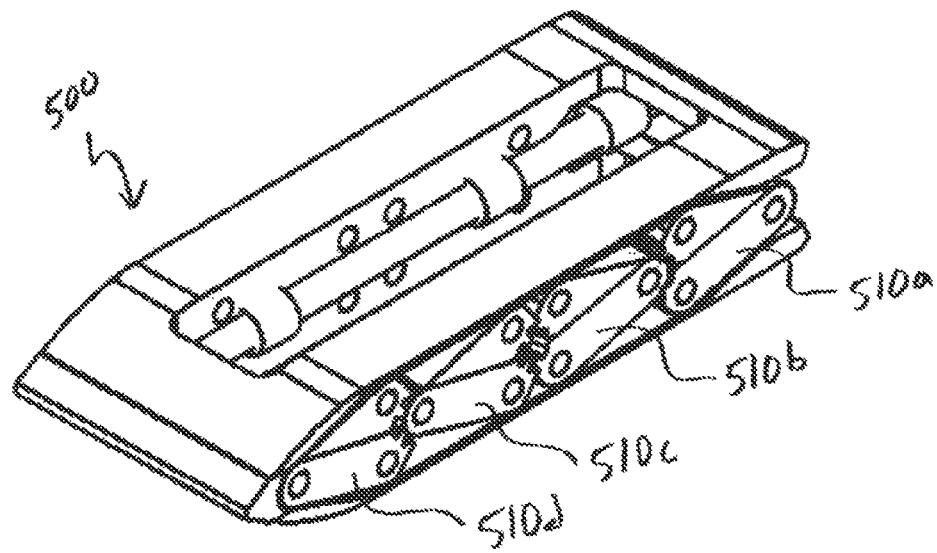
FIG. 10A is a perspective view of a distractible intervertebral body fusion device according to an aspect of the present invention.
Figure 10B:
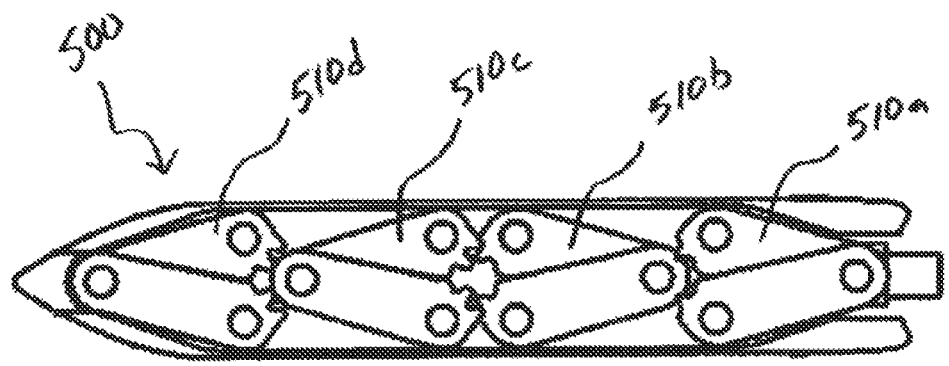
FIG. 10B is a side view of the distractible intervertebral body fusion device of FIG. 10A.
Figure 11A:
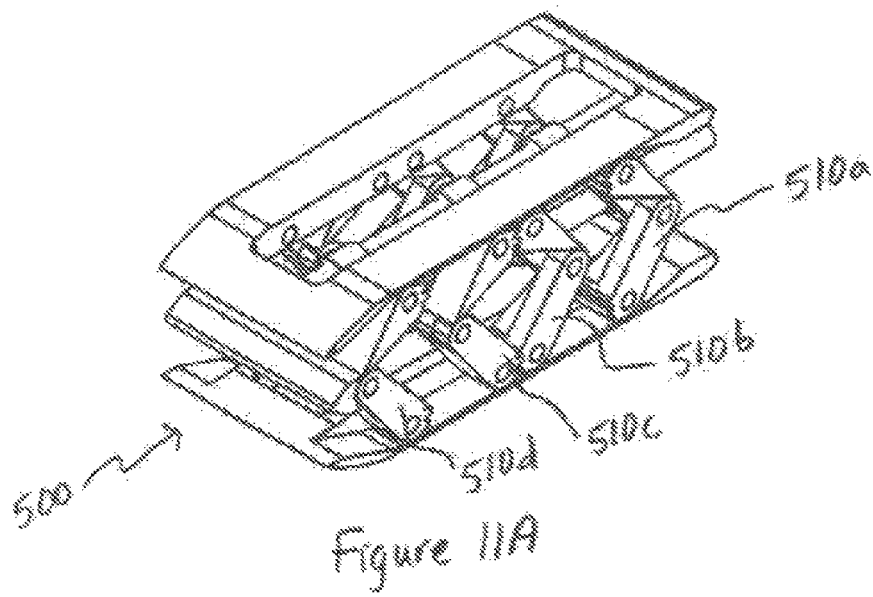
FIG. 11A is a perspective view of the distractible intervertebral body fusion device of FIG. 10A in an expanded configuration.
Figure 11B:
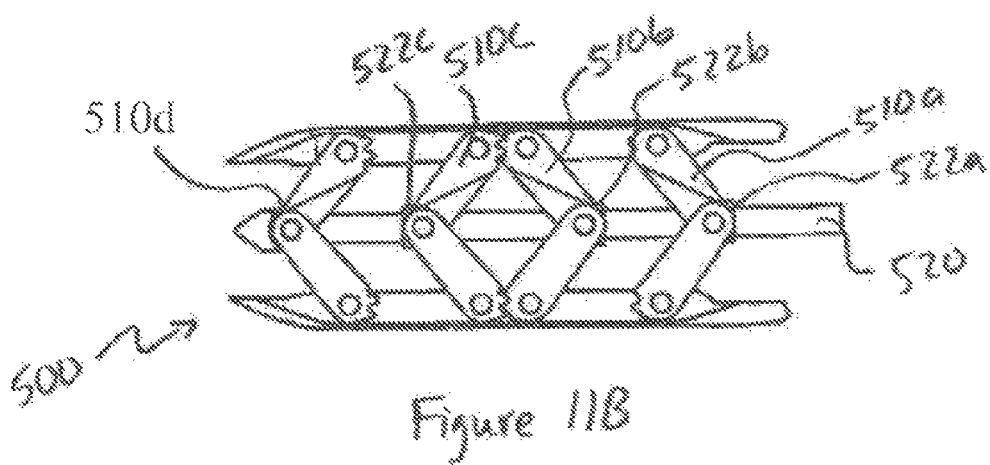
FIG. 11B is a side view of the distractible intervertebral body fusion device of FIG. 10A in an expanded configuration.
Figure 11C:
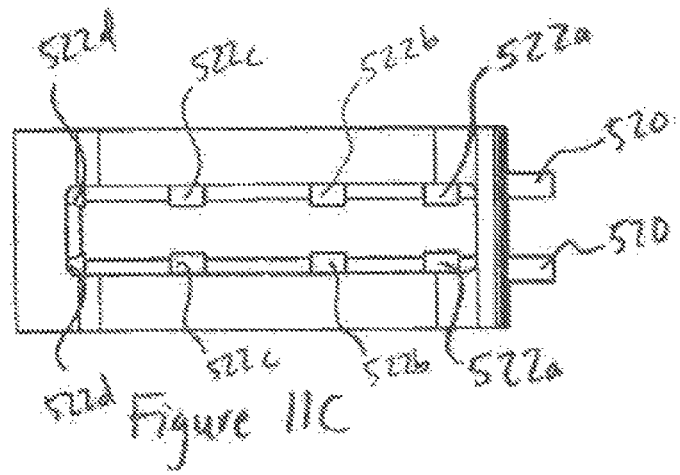
FIG. 11C is a top view of the distractible intervertebral body fusion device of FIG. 10A in an expanded configuration.

Device 300 can include a third arm 310c in addition to a first arm 310a and second arm 310b. In one embodiment, third arm 310c is attached to base plates 308 with the same pins 314 as second arm 310b. In another embodiment, third arm 310c is separately hinged to base plates 308. Third arm 310c can be positioned at any point along base plates 108 between nose portion 304 and rear portion 306. Third arm 310c provides a means for stably maintaining the device 300 under in-vivo loads when in a distracted position. As is demonstrated by a simplified form of device 300 shown in FIG. 7, device 300 can stably support the disc space because it has zero degrees of freedom once locked in the distracted position with threaded members 320 in place. From Gruebler's equation, the number of degrees of freedom=$3*(n-1)-2f$, where n is the number of links 360 in the linkage and f is the number of one degree of freedom kinematic pairs 362 in the linkage. As is shown in FIG. 7, the device 300 has 9 links and 12 kinematic pairs, so $3*(9-1)-2*12=0$ degrees of freedom.

Optionally, and in the example of embodiment 300 where the rigid links 310c and 310b share a common hinge 314, the rigid link 310a may be slightly longer than either 310c or 310b thus resulting in the rear portion 306 of the device 300 having a distracted height that is slightly greater than the distracted height of the nose portion 304 of the device 300. Additionally block 322a may be supplemented with a differential screw mechanism that would allow the position of block 322a to be independently controlled with respect to block 322b. Such control of 322a would allow the lordosis, or angular orientation of the endplates, to be matched exactly to the unique lordosis, or desired lordosis, of a patient's spine. Specifically, the differential screw mechanism would be accomplished by threading an internally and externally threaded cylinder over the threaded member 320 but within the block 322a. The threaded cylinder could then be removably coupled to an external drive device as threaded member 320 is removably coupled to insertion tool 350.

Additionally, with embodiment 300, when portions of the threaded members are not reverse threaded and clearance exists in block 322c the device may be able to be gently and additionally distracted due to in-vivo axial tension as the clearance in block 322c allows block 322c to slide closer to block 322b and block 322a. However, having distracted slightly under tensile loading the device would return to the original height as compressive loading is returned. The parallelism would remain unchanged, while lordotic endplates may undergo a small angular displacement that would return to the set lordosis with the reapplication of the normal compressive loading. This extensibility of the device could offer great benefits to the fusion process as the endplates, which may be growing into the endplates of the vertebral bodies, would not be pulled away, damaging early bone growth, from the endplates by motion of the patient's spine.

Figure 6A:
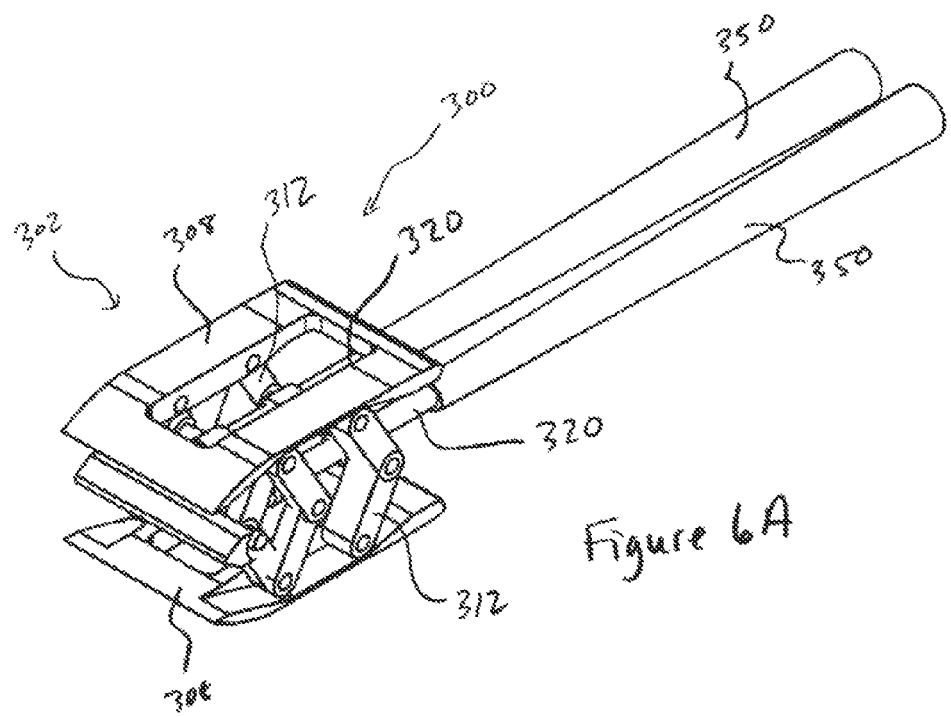
FIG. 6A is a perspective view of the distractible intervertebral body fusion device of FIG. 5A in an expanded configuration.
Figure 6B:
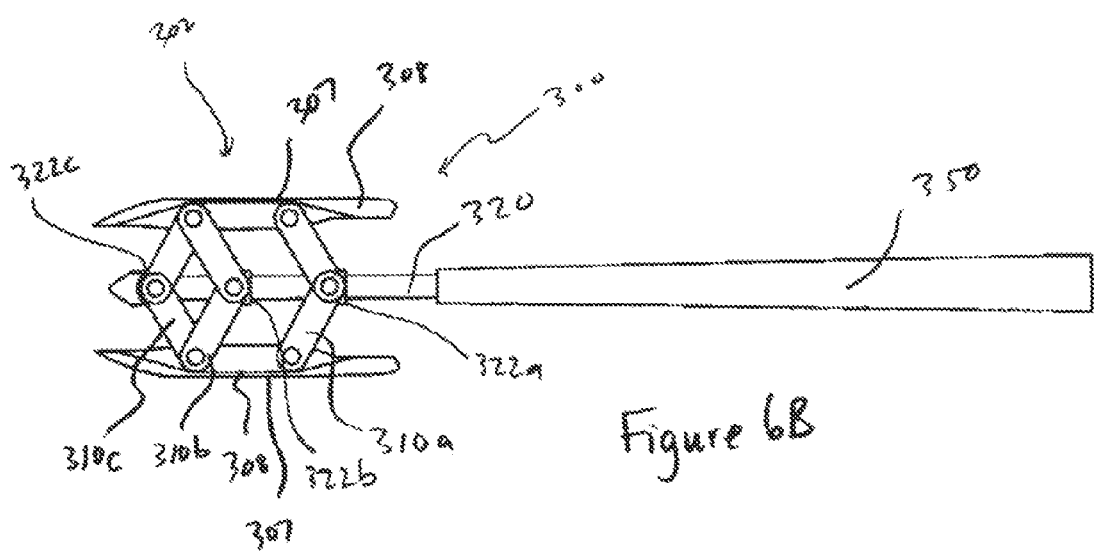
FIG. 6B is a side view of the distractible intervertebral body fusion device of FIG. 5A in an expanded configuration.

As with device 100 and device 200, threaded members 320, such as screws, and insertion tool 350 can be used to distract device from the compressed state shown in FIGS. 5A and 5B to a distracted state, such as the one shown in FIGS. 6A and 6B. Because device 300 has three arms 310, threaded members 320 are inserted through first blocks 322a attached to the first arms 310a, through second blocks 322b attached to the second arms 310b, and into third blocks 322c attached to the third arms 310c. Actuation of threaded members 320 in a first direction drives blocks 322 closer together, which causes expansion of arms 310 and distraction of base plates 308. Actuation of threaded members 320 in the opposite direction would drive blocks 322 apart, thereby bringing base plates 308 closer together. In one embodiment, blocks 322a and 322b can be tapped to accommodate threaded members 320 and blocks 322c can provide a clearance fit with threaded members 320. When threaded members 120 are actuated, this allows blocks 322c to be pulled towards blocks 322a, 322b, causing the device 300 to distract.

In another embodiment depicted in FIGS. 10A-10B and 11A-11C, a distractible intervertebral body fusion device 500 can include a fourth arm 510d in addition to first 510a, second 510b, and third 510c arms. Device 500 can also include a corresponding fourth block 522d connected to fourth arm 510d in addition to first 522a, second 522b, and third 522c arms through which threaded members 520 extend. The device 500 is also capable of stably supporting the disc space. In fact, the device 500 is actually overconstrained in that it has additional constraints (i.e., a fourth arm 510d) over and above what is necessary to constrain the device 500 to have zero degrees of freedom.

Referring now to FIGS. 8A-8B and 9A-9B there can be seen a further embodiment of a distractible intervertebral fusion device 400 according to an aspect of the present invention. Device 400 includes a device body 402 including a nose portion 404, a rear portion 406, a pair of opposed base plates 408 having outer bearing surfaces 407, and arms 410. Device 400 can have arms 410 on both side 416, 418 of device 400.

Arms 410 of device 400 are hingedly attached to each other with a pin 414. In one embodiment, arms 410 comprise a single structural member 412 and form a generally x-shape with each other. Each arm 410 has one end hingedly attached to one of the base plates 408 and the other end slidably attached to a slot 409 in the opposite base plate 408. As with the previously described devices, the device 400 is distracted from the compressed configuration shown in FIGS. 8A and 8B to an expanded configuration such as the one shown in FIGS. 9A and 9B by rotating a threaded member 420 within blocks 422 attached to arms 410. In this embodiment, as the blocks 422 are drawn closer together, the pins 414 slidably disposed within slots 409 translate within slots 409 from an end nearest the nose portion 404 towards an end nearest the rear portion 406 to allow arms 410 to expand, which causes base plates 408 to distract. This device also stably supports the disc space. The device has four rigid links, two one-degree of freedom kinematic pairs (pinned joints), and two two-degree of freedom kinematic pairs (slidably disposed joints) that may be locked in place within the slots 409 making them one degree of freedom kinematic pairs. Prior to locking the pins within slots, the device would have $3(4-1)-2(3)-1(2)=1$ degree of freedom and post locking the device would have $3(4-1)-2(5)=-1$ degree of freedom. Additionally, the slidably disposed joints could be considered to be axially locked at all times while mounted on the threaded members 420 thus having $3(4-1)-2(5)=-1$ degree of freedom and exhibiting stability.

Optionally, the device 400 could be constructed such that both ends of each arm 410 and the pins 414 to which the arms 410 are affixed are slidably disposed within a broader slot 409 and the arm assembly remains centered along the length of the device by translationally fixing the threaded member 420 along its length while allowing it to rotate. As in previous optional embodiments, portions of the threaded member 420 could be reverse threaded such that turning the threaded member 420 would move threaded block 422 and its reverse threaded complement towards each other. Additionally a hybrid of this embodiment 400 and the embodiment 100 presented in FIG. 1A could be created such that the slidably disposed mechanism of embodiment 400 could be implemented as the drive mechanism on the bottom plate 408 and the pinned hinges 114 with gear teeth 111 can be used as the means of stabilizing the top plate 108. In this hybrid design the links may not be crossed as in the embodiment 400. Instead, the links could be configured similarly to a horizontally mirrored pair of links 112 of embodiment 100.

Referring again to FIGS. 8A-8B and 9A-9B, in certain embodiments, devices can also include pins 415 extending vertically through devices and slidably disposed within or relative to one of the endplates, either top or bottom, of the device. Pins 415 add torsional stiffness to the device to help keep the end plates parallel during distraction. Pins can be of any shape, such as for, example, rectangular, circular, elliptical, oblong, or hexagonal. In-vivo torsion may be one of the major challenges prohibiting the successful approval and market release of low-profile distractable fusion-devices. In-vivo dynamic torsional loading may exceed 10 [Nm] and static torsional loading may exceed 10-20 [Nm]. A device having titanium (or exhibiting the mechanical properties of common medical grade alloys of titanium) pins mounted vertically at the four corners of the device, when viewed from the top, each approximately 15 [mm] from the vertical axis of torsion of the device would require pin diameters of 2-3 [mm] to prevent the device from deflecting more than 1 [deg] due to said torsional loading. Without pins, sustaining nearly 5 million cycles of 10 [Nm] torsional loading could cause serious failure to any device with intricate welds and the inevitable stress risers inherent to the small radii and tight curvatures inherent to complex micro-machined components. The pins also help to support the in-vivo dynamic shear load which can be greater than 600 to 750 [N] with an additional and often equal, in magnitude, compressive component. Although depicted as having four pins at the corners of the device, it should be understood that different numbers of pins in various locations can be utilized.

Although the various devices described herein are described as being brought from a compressed configuration to an expanded configuration by rotation of a threaded member, the devices can be distracted by any other type of actuation member. In some embodiments, mechanisms other than threaded members can be used to distract the device. Such mechanisms include, for example, a pop-rivet mechanism, a sardine key and ribbon, a tourniquet and wire, a saw blade/ratchet, a zip-tie-like mechanism, piezo-electric inch worm motors and shape changing materials such as a shape member alloy or a conducting polymer actuator. These alternative locking mechanisms could be designed to make the device behave as if it were locked with a threaded member, preventing the device from being compressed as well as extended, or these mechanisms could afford the device the capability to ratchet upwards post implantation if such action would benefit the patient or provide additional therapy.

Various embodiments of implantation procedures for the disclosed embodiments of distractible intervertebral fusion devices may be as follows:

Lumbar: A lumbar implant can be 6 mm in height, expandable to 12 mm in height, with a length of 25-30 mm and a width of 6 mm. The implant can be inserted through a minimally invasive tubular port that goes through the muscle of the lumbar spine and into the lumbar disc space. Prior to inserting the implant, the lumbar disc should be completely removed.

Cervical: A cervical implant can be 6 mm in height, expandable to 10 mm in height, with a length of 10 mm and a width of 6 mm. The implant can be inserted after anterior cervical surgical exposure. The cervical disc should be completely removed prior to insertion of the implant.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

The invention claimed is:

1. A distractible intervertebral body fusion device adapted to be implanted into an intervertebral disc space in a patient's body, comprising:
    a first base plate having an outer bearing surface configured to interface with a first vertebra of the intervertebral disc space;
    a second base plate having an outer bearing surface configured to interface with a second vertebra of the intervertebral disc space;
    a plurality of blocks disposed between the first base plate and the second base plate, each block having an aperture therethrough;
    an arm assembly extending between the first base plate and the second base plate on each of a first side and a second side of the base plates, each arm assembly comprising:
        a first arm comprising first and second structural members, the first structural member hingedly attached at one end to one of the first base plate and the second base plate and at an opposing end to one of the blocks, and the second structural member hingedly attached at one end to the other of the first base plate and the second base plate and at an opposing end to the one of the blocks to which the first structural member is attached;
        a second arm directly adjacent to the first arm and comprising third and fourth structural members, the third structural member hingedly attached at one end to one of the first base plate and the second base plate and at an opposing end to one of the blocks, and the fourth structural member hingedly attached at one end to the other of the first base plate and the second base plate and at an opposing end to the one of the blocks to which the third structural member is attached; and
        a third arm linearly displaced from the first arm and the second arm and comprising fifth and sixth structural members, the fifth structural member hingedly attached at one end to one of the first base plate and the second base plate and at an opposing end to one of the blocks, and the sixth structural member hingedly attached at one end to the other of the first base plate and the second base plate and at an opposing end to the one of the blocks to which the fifth structural member is attached; and
    first and second actuation members, the first actuation member adapted to extend through the apertures of a plurality of the blocks attached to the first, second and third arms of the arm assembly on the first side of the base plates and the second actuation member adapted to extend through the apertures of a plurality of the blocks attached to the first, second and third arms of the arm assembly on the second side of the base plates, each actuation member independently operable to drive the respective blocks closer together to expand the respective arms to cause the first base plate and the second base plate to move away from each other into a distracted position, and
    wherein one or more blocks adjacent a common side of the first side and the second side of the base plates are separately driveable with the respective actuation member with respect to the other blocks on the common side such that the corresponding arms on the common side can be expanded by different amounts to position at least one of the first and second base plates in a lorditically angled configuration adapted to match a unique lordosis of a specific patient.

2. The device of claim 1, wherein each actuation member is a threaded member such that rotation of each actuation member in a first direction within the respective blocks causes the respective arms to expand and rotation of each actuation member in a second direction within the respective blocks opposite of the first direction causes the respective arms to collapse.

3. The device of claim 1, wherein the first arm and the second arm abut each other.

4. The device of claim 3, wherein the one end of the first structural member hingedly attached to the one of the first base plate and the second base plate abuts the one end of the third structural member hingedly attached to the one of the first base plate and the second base plate and the one end of the second structural member hingedly attached to the other of the first base plate and the second base plate abuts the one end of the fourth structural member hingedly attached to the other of the first base plate and the second base plate.

5. The device of claim 1, wherein each of structural members is hingedly attached to the respective first base plate or second base plate with a pin and further hingedly attached to the respective block with a pin.

6. The device of claim 5, wherein the first structural member and third structural member are attached to the one of the first base plate and the second base plate with separate pins and the second structural member and fourth structural member are attached to the other of the first base plate and the second base plate with separate pins.

7. A distractible intervertebral body fusion device adapted to be implanted into an intervertebral disc space in a patient's body, comprising:
    a first base plate;
    a second base plate;
    a first arm on each of a first side and a second side of the base plates extending between the first base plate and the second base plate, each first arm hingedly attached at one end to the first base plate and at an opposing end to the second base plate;

a second arm directly adjacent to the first arm on each of the first side and the second side of the base plates extending between the first base plate and the second base plate, each second arm hingedly attached at one end to the first base plate and at an opposing end to the second base plate; and a third arm linearly displaced from the first arm and the second arm on each of the first side and the second side of the base plates extending between the first base plate and the second base plate, each third arm hingedly attached at one end to the first base plate and at an opposing end to the second base plate; and first and second actuation members extending axially between the first base plate and the second base plate, each actuation member independently rotatable between the first base plate and the second base plate to expand the first, second and third arms on a respective side of the base plates to cause the first base plate and the second base plate to move away from each other into a distracted position, and wherein at least two of the first arm, second arm and third arm on each of the sides of the base plates are separately expandable with respect to each other with the respective actuation member such that the arms can be expanded by different amounts to position at least one of the first and second base plates in a lordotically angled configuration adapted to match a unique lordosis of a specific patient.

8. The device of claim 7, wherein each actuation member is a threaded member such that rotation of each actuation member in a first direction causes the respective arms to expand and rotation of each actuation member in a second direction opposite of the first direction causes the respective arms to collapse.

9. The device of claim 7, wherein the first arm and the second arm abut each other.

10. The device of claim 9, wherein the one end of the first arm hingedly attached to the first base plate abuts the one end of the second arm hingedly attached to the first base plate and the opposing end of the first arm hingedly attached to the second base plate abuts the opposing end of the second arm hingedly attached to the second base plate.

11. The device of claim 7, wherein each of the arms is hingedly attached to the first base plate with a pin and to the second base plate with a pin.

12. The device of claim 11, wherein the first arm and the second arm are hingedly attached to the first base plate with separate pins and to the second base plate with separate pins.

13. The device of claim 7, wherein each arm comprises two structural members.

14. A distractible intervertebral body fusion device adapted to be implanted into an intervertebral disc space in a patient's body, comprising:

a first base plate having an outer bearing surface configured to interface with a first vertebra of the intervertebral disc space and first and second sides;

a second base plate having an outer bearing surface configured to interface with a second vertebra of the intervertebral disc space and first and second sides;

a pair of first arms extending between and hingedly attached to the first base plate and the second base plate, one of the first arms on each of the first and second sides of the base plates;

a pair of second arms extending between and hingedly attached to the first base plate and the second base plate, one of the second arms on each of the first and second sides of the base plates, wherein the first pair of arms and second pair of arms are expandable between a collapsed configuration and an expanded configuration in which the first base plate and the second base plate are distracted with respect to each other;

a pair of stabilizing arms extending between and hingedly attached to the first base plate and the second base plate, one of the stabilizing arms on each of the first and second sides of the base plates;

a pair of actuation members, each actuation member extending adjacent one of the first and second sides of the base plates and independently rotatable to expand the first, second and stabilizing arms along the respective side of the base plates to distract the base plates with respect to each other; and wherein the stabilizing arms are adapted to stably maintain the base plates in the distracted position under in-vivo loads with zero degrees of freedom, and wherein at least two of the first arm, second arm and stabilizing arm on each of the sides of the base plates are separately expandable with respect to each other with the respective actuation member such that the arms can be expanded by different amounts to position at least one of the first and second base plates in a lordotically angled configuration adapted to match a unique lordosis of a specific patient.

15. The device of claim 14, further comprising a plurality of blocks positioned between the first base plate and the second base plate, each block operably connected with at least one of the arms, and wherein the actuation members each extend through at least some of the blocks.

16. The device of claim 14, wherein each actuation member is a threaded member such that rotation of each actuation member in a first direction causes the respective arms to expand and rotation of each actuation member in a second direction opposite of the first direction causes the respective arms to collapse.

17. The device of claim 14, wherein each arm comprises two structural members.

* * * * *